US 6,527,748 B1

(12) United States Patent
Suzuki

(10) Patent No.: US 6,527,748 B1
(45) Date of Patent: Mar. 4, 2003

(54) METHOD OF GASTROSTOMY, AND AN INFECTION PREVENTIVE COVER, KIT OR CATHETER KIT, AND A GASTROSTOMY CATHETER KIT

(76) Inventor: Yutaka Suzuki, 1-2, Hakusan 2-chome, Guran Aruba Hakusan 601, Bunkyou-ku, Tokyo 112-0001 (JP)

( * ) Notice: Subject to any disclaimer, the term of this patent is extended or adjusted under 35 U.S.C. 154(b) by 0 days.

(21) Appl. No.: 09/574,452

(22) Filed: May 19, 2000

Related U.S. Application Data

(63) Continuation-in-part of application No. 09/375,374, filed on Aug. 17, 1999, now abandoned.

(30) Foreign Application Priority Data

Aug. 17, 1998 (JP) .............................. 10-231041
Aug. 17, 1999 (JP) .............................. 11-230252
Feb. 18, 2000 (JP) ........................... 2000-041940

(51) Int. Cl.⁷ ................................................ A61M 5/00
(52) U.S. Cl. ............... 604/171; 604/910; 128/DIG. 24; 128/842; 383/76; 383/200
(58) Field of Search ................................ 604/910, 163, 604/103.05, 171, 198; 128/DIG. 18, DIG. 24, 842, 844, 918; 606/110, 113; 383/76, 200, 202; 600/38

(56) References Cited

U.S. PATENT DOCUMENTS

| | | | | |
|---|---|---|---|---|
| 5,181,913 A | * | 1/1993 | Erlich | 600/562 |
| 5,279,539 A | * | 1/1994 | Bohan et al. | 600/37 |
| 5,312,416 A | * | 5/1994 | Spaeth et al. | 600/562 |
| 5,336,193 A | * | 8/1994 | Rom et al. | 604/171 |
| 5,505,714 A | * | 4/1996 | Dassa et al. | 604/163 |
| 5,582,165 A | * | 12/1996 | Bryan et al. | 128/207.14 |
| 5,666,971 A | * | 9/1997 | Anatolievich | 128/842 |
| 5,785,677 A | * | 7/1998 | Auweiler | 128/850 |
| 5,803,085 A | * | 9/1998 | Asinovsky | 128/844 |
| 6,206,889 B1 | * | 3/2001 | Bennardo | 128/DIG. 24 |
| 6,308,709 B1 | * | 10/2001 | Paul | 128/844 |

FOREIGN PATENT DOCUMENTS

EP        0 744 185 A1 * 11/1996 .......... A61M/25/01

* cited by examiner

Primary Examiner—Brian L. Casler
Assistant Examiner—Mark Han
(74) Attorney, Agent, or Firm—McGinn & Gibb, PLLC

(57) ABSTRACT

An infection preventive cover includes a sheath having at least one opening end, a binding thread to close the opening end of the sheath, and a cutting thread linked to the binding thread, the cutting thread being stronger than the binding thread.

4 Claims, 36 Drawing Sheets

*Fig.23*
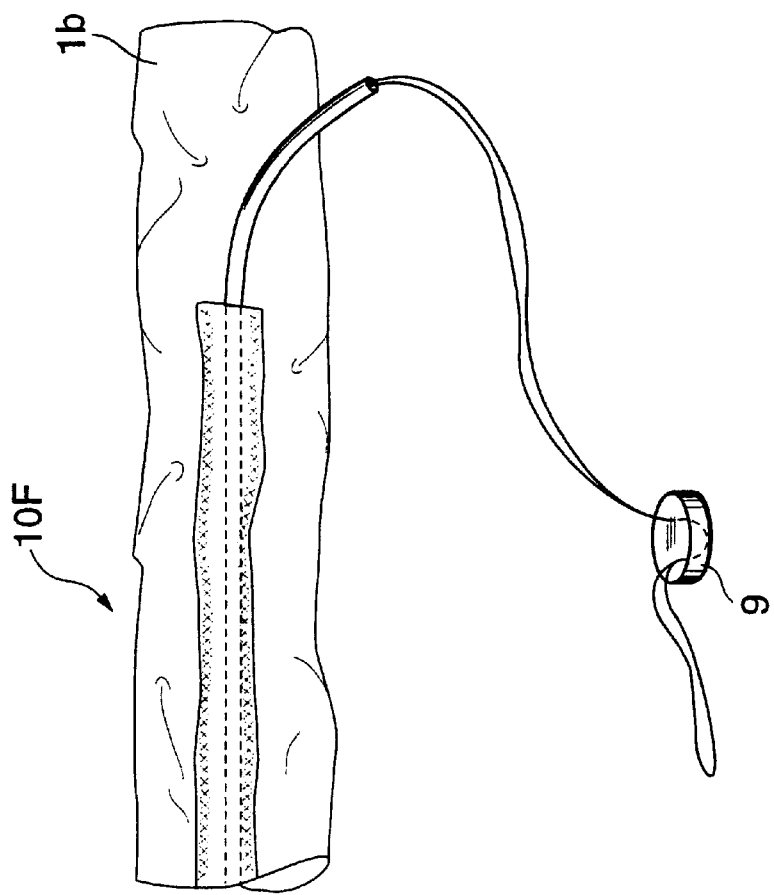
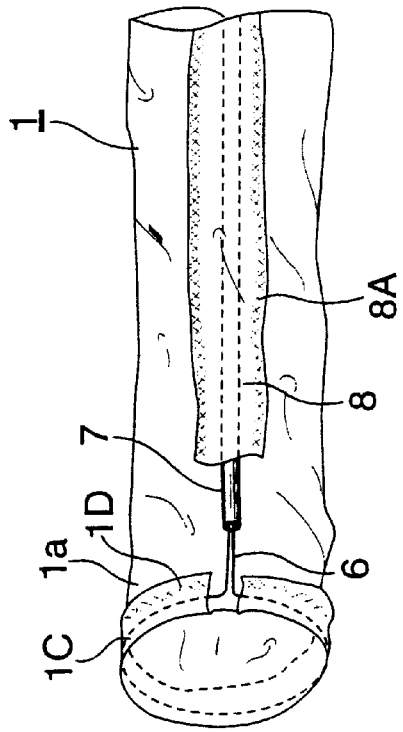

METHOD OF GASTROSTOMY, AND AN INFECTION PREVENTIVE COVER, KIT OR CATHETER KIT, AND A GASTROSTOMY CATHETER KIT

The present invention is related to and is a continuation-in-part of U.S. patent application Ser. No. 09/375,374, filed on Aug. 17, 1999, now abandoned and entitled "A METHOD OF GASTROSTOMY, AND AN INFECTION PREVENTIVE COVER AND A GASTROSTOMY CATHETER KIT" by Yutaka Suzuki.

BACKGROUND OF THE INVENTION

1. Field of the Invention

The present invention relates to a method of gastrostomy, and an infection preventive cover, kit or catheter kit and a gastrostomy catheter kit for use with the method.

2. Description of the Related Art

For a percutaneous endoscopic gastrostomy (PEG) enabling enteral feeding of a patient who finds swallowing food difficulty or who cannot swallow, it is sufficient to apply a local anethesia to the patient and the operation time is favorably short, i.e., about five to about ten minutes, and the patient can quickly recover after the operation. In a case where the patient in a good general condition after the operation, she or he may leave the hospital on the same day on which the operation is conducted. The PEG and its use has therefore developed rapidly worldwide. In the United States, for example, about 180,000 cases were reported in 1997. In the future, the number of the operations is in the world is expected to increase.

As commonly known, the PEG includes three methods, namely, "pull", "push", and "introducer" methods (techniques). Among these methods, the "pull" and "push" methods have been broadly adopted due to simplicity and safety of the operation. However, these methods include the drawbacks described below.

The endoscope is required to be twice inserted in the pertinent patient, which leads to a problem of complex operations and pain to patients. There exists a fear of damage to the larynx, the upper pharynx or the esophagus.

The PEG catheter (including a PEG tube and a dome connected to the tube) is infected in the oral cavity, the upper pharynx or the larynx and hence the wounded part of the patient is liable to be infected.

The first drawback above can be overcome by improving the sedation or anesthesia and by increasing the quality of skill of the endoscopist. However, the second drawback, i.e., the infection of the wound due to the contamination of the PEG tube and the dome has a high possibility of occupancy. The literature from Europe and America reported about 35% to about 45% of the infection of wound. When the infection of a wound occurs, antibiotics are required to be administered to the patient for a long period of time. This resultantly delays the starting point of the enteral feeding for the patient, and the immunity of the patient from diseases is weakened, this may lengthen the hospital treatment in some cases. The patient suffers from serious pains and the fee for medical treatment soars. Consequently, not only the patient but also family members of the patient must bear the expense and suffer from mental stress. When the cleaning of the oral cavity, the preoperation disinfection of the upper pharynx, and the preventive administration of antibiotics are completely carried out, the number of bacteria appearing on the PEG tube and the dome can be decreased. However, this is not the basic countermeasure.

SUMMARY OF THE INVENTION

It is therefore an object of the present invention to provide a method of gastrostomy capable of preventing the infection of a wound.

Another object of the present invention is to provide an infection preventive cover to prevent the infection of a wound in the method of gastrostomy.

Still another object of the present invention is to provide a gastrostomy catheter (PEG catheter) kit to prevent the infection of a wound in the method of gastrostomy.

Still another object of the present invention is to provide an infection preventive kit to prevent the infection of a wound in the method of gastrostomy.

Yet another object of the present invention is to provide an infection preventive catheter kit to prevent the infection of a wound in the method of gastrostomy.

Further another object of the present invention is to provide a gastrostomy catheter (PEG catheter) used in the method of gastrostomy which exhibits fine performance.

A method of gastrostomy in accordance with the present invention includes inserting a guide wire into a stomach through an outer tube pierced through a wall of an abdomen and a wall of the stomach of a patient and pulling the guide wire through an esophagus and an oral cavity into a space outside the patient, joining one end of a percutaneous endoscopic gastrostomy (PEG) catheter with the guide wire, delivering the PEG catheter into the stomach by pulling ("pulling method") or pushing ("pushing method") the guide wire, drawing the PEG catheter together with the outer tube through a hole in the wall of the stomach and the abdomen wall into a space outside the patient, keeping another end of the PEG catheter in the stomach (including a case in which the end is cut away from the catheter), characterized by enclosing entirely the PEG catheter with an infection preventive cover having a sheath, the sheath having one opening end, closing the opening end of the sheath in the vicinity of the position of a joint between the PEG catheter and the guide wire, delivering the PEG catheter through the oral cavity into the stomach with the PEG catheter covered with the infection preventive cover, opening the opening end of the sheath in the stomach, drawing the PEG catheter into a space outside the patient, while drawing the PEG catheter through the opening end of the sheath opened, and removing thereafter the infection preventive cover from the oral cavity into a space outside the patient. The present invention is applicable to either the "push method" or the "push method" of gastrostomy.

In accordance with the present invention, the PEG catheter and the joint section between the PEG catheter and the guide wire are covered outside the oral cavity with the infection preventive cover having a sheath to be delivered from the oral cavity into the stomach in the covered state. Since the opening end of the infection preventive cover is closed until the cover reaches the stomach, the PEG catheter does not directly contact the oral cavity, the larynx and the upper pharynx of the patient. The PEG catheter is therefore kept clean.

The opening end of the infection preventive cover is opened in the stomach of the patient, and the PEG catheter is withdrawn through the opening end of the cover and is drawn through a hole (wounded part of the patient) prepared in the abdominal and stomach walls into a space outside the patient. When the PEG catheter is delivered into the stomach, the catheter is kept clean, namely, is not inflected. Even when the clean PEG catheter is brought into contact with the hole (wound) in the abdominal and stomach walls, the hole (wound) is hardly inflected. Consequently, infection of the wound can be efficiently prevented.

An infection preventive cover in accordance with the present invention is used in the gastrostomy and comprises an elongated sheath having at least one opening end, a binding thread embroidered along a circumferential edge of the opening end of the sheath, and a cutting thread linked to the binding thread, the both ends of the binding thread being led outside the sheath at positions near to each other, and the cutting thread being stronger than the binding thread.

There can be considered various kinds of embroidering of the binding thread (a ligature) in the opening end of the sheath. For example, the ligature is reciprocally embroidered with an appropriate interval between an inner side and an outer side of the opening end portion of the sheath. Alternatively, the opening end portion of the sheath is folded back and the folded-back edge is fixed to the sheath by welding, melting or the like to thereby produce a threading bag, pass or guide, and the ligature is passed through the threading bag.

The cutting thread also includes a thread made of metal such as a metallic wire. Any chemical fiber such as nylon may be used if the cutting thread is stronger than the ligature. The sentence "a cutting thread is linked to the binding thread" includes a state in which the cutting thread is doubled to simply engage with the ligature.

For the infection preventive cover (the sheath), there is favorably employed thin, airtight, waterproof, flexible and strong materials such as vinyl and rubber. The PEG catheter may be covered with the infection preventive cover by inserting the PEG catheter into the elongated sheath.

Since the ligature is provided beforehand in the sheath, the operator need only bind the ligature to close the opening end of the sheath. Another method may also be adopted by use of the ligature to close the opening end. The operator need not be skillful with fingers to attach the sheath, and the gastrostomy can be hence completed in a short period of time.

The PEG catheter is entirely covered with the sheath of the infection preventive cover in accordance with the present invention. Consequently, the infection of the wound can be prevented in the gastrostomy. The cutting thread can be drawn through the outer tube punctured into the abdomen wall or through the sheath into a space outside the patient. Consequently, by drawing the cutting thread to cut the ligature, it is possible to open the opening end of the sheath in the stomach.

An infection preventive cover kit in accordance with the present invention, includes an elongated sheath having at least one opening end, a binding thread (a ligature) to close the opening end of the sheath, and a cutting thread linked to the binding thread, the cutting thread being stronger than the binding thread.

The binding thread (a ligature) may be attached onto the sheath or may be separated therefrom. In either case, the opening end of the sheath covering the PEG catheter can be bound by the ligature into a closed state thereof. In the stomach, the ligature is cut by the cutting thread to thereby open the opening end of the sheath.

The present invention provides a PEG catheter kit utilizing the above infection preventive cover or the infection preventive cover kit. The PEG catheter kit comprises a PEG catheter, a sheath, into which the PEG catheter has been inserted, having at least one opening end, a binding thread to close the opening end of the sheath, and a cutting thread linked to the binding thread, the cutting thread being stronger than the binding thread. Since the PEG catheter has been covered with the sheath, a work for covering the PEG catheter with the sheath can be dispensed with. This also minimizes the period of time necessary for the gastrostomy. The opening end of the sheath covering the PEG catheter can be bound by the binding thread into a closed state thereof. By drawing the cutting thread, the binding thread is cut by the cutting thread to thereby open the opening end of the sheath in the stomach.

In one embodiment, the binding thread is embroidered along a circumferential edge of the opening end of the sheath, and the both ends of the binding thread are led outside the sheath at positions near to each other.

A PEG catheter kit in accordance with the present invention includes a PEG catheter, an elongated sheath entirety enclosing the PEG catheter, a fixing device integrally provided to an end of the sheath, an end of the PEG catheter being arranged at the fixing device, and a breaking thread for breaking a portion of the fixing device and a portion of the sheath. Since the PEG catheter has been covered with the sheath, a work for covering the PEG catheter with the sheath can be dispensed with. This also minimizes the period of time necessary for the gastrostomy. Moreover, it may also be possible that the breaking thread is drawn through an outer tube pierced through the abdomen wall or through the sheath into a space outside the patient such that at least the fixing device (and favorably, a part of the sheath) is broken or cut away by the breaking thread in the stomach to open the opening end of the sheath so as to withdraw the PEG catheter out of the sheath.

Another PEG catheter kit in accordance with the present invention includes a PEG catheter, a sheath substantially enclosing the PEG catheter, an end of the sheath being closed, and a breaking thread, an end portion of which is fixed to the closed end portion of the sheath, for breaking the closed end portion of the sheath when the other end of the breaking thread is pulled. Since the PEG catheter has been covered with the sheath, a work for covering the PEG catheter with the sheath can be dispensed with. Moreover, it may also be possible that the breaking thread is drawn through an outer tube pierced through the abdomen wall or through the sheath into a space outside the patient such that a part of the sheath is cut away by the breaking thread in the stomach to open the opening end of the sheath so as to withdraw the PEG catheter out of the sheath.

In one embodiment, the catheter includes a joint wire extending from a top of the catheter, and the end of the sheath closes at a position of the joint wire. Preferably, a part of the joint wire which is exposed outside of the sheath is sufficiently disinfected before use.

An infection preventive cover according to the present invention includes a sheath having at least one opening end, a closing thread embroidered along a circumferential edge of the opening end of the sheath, and a tube for tightening. Two portions of the closing thread having ends are apart from the embroidered portion thereof at positions near to each other. The tightening tube is disposed such that one end of the tube is in the vicinity of the embroidered portion. At least one portion of the closing thread is inserted into the one end of the tightening tube and passes loosely through inside of the tightening tube to be led outside from the other end of the tightening tube.

There can be considered various kinds of embroidering of the closing thread in the opening end of the sheath. For example, the opening end portion of the sheath is folded back and the folded back edge is fixed to the sheath by welding, melting or like to thereby produce a threading bag, pass or guide, and the closing thread is passed through the threading bag. Alternatively, the closing thread is reciprocally embroidered with an appropriate interval between an inner side and an outer side of the opening end portion of the sheath. The closing thread may be turned back on the circumferential edge of the opening end of the sheath, that is, the closing thread is formed to be a loop along the opening end of the sheath, and the two portions having ends may be passed through the tightening tube to be led outside of the tightening tube. Alternatively, the closing thread may be turned back on the circumferential edge of the opening end of the sheath, an end of a portion of the closing thread may be fixed to the one end of the tightening tube, and the other portion of the closing thread having the other end may be passed through the tightening tube to be led outside. Further the closing thread may be turned back on the circumferential edge of the opening end of the sheath, an end of a portion of the closing thread my be fixed to a ring, and the other portion of the closing thread having the other end may be passed through the ring and further through the tightening tube to be led outside.

Preferably, the tightening tube extends along the sheath in the longitudinal direction thereof. The tightening tube may be disposed along inside of the sheath or along outside of the sheath. The sheath may be provided with a cover and the tightening tube extending along the longitudinal direction of the sheath is covered with the cover except for at least the other end of the tightening tube. The cover may be welded, meted or adhered to be fixed to the sheath at both sides thereof, so that a bag, pass or guide is formed by the cover and the sheath, into which the tightening tube is inserted. The cover itself may be a bag.

The sheath is longer than the distance from the stomach to mouth of a patient and has an enough length to entirely cover a percutaneous endoscopic gastrostomy catheter (PEG catheter). The tightening tube may be shorter than the sheath, and is sufficient to have the length from the stomach to mouth of the patient.

For the infection preventive cover (the sheath), there is favorably employed thin, airtight, waterproof, flexible and strong materials such as vinyl and rubber. The PEG catheter may be covered with the infection preventive cover by inserting the PEG catheter into the elongated sheath.

For the closing thread, materials such as silk, linen, cotton, polyester, polyethylene and any other vegetable fiber, chemical fiber or metal materials may be used.

The infection preventive cover in accordance with the present invention is used in a method of gastrostomy as follows;

In the method of gastrostomy a guide wire is inserted into a stomach through an outer tube pierced through a wall of an abdomen and a wall of the stomach of a patient. The guide wire is pulled through an esophagus and an oral cavity into a space outside the patient. One end (a conical top portion) of a percutaneous endoscopic gastrostomy (PEG) catheter is joined with the guide wire. The PEG catheter is delivered from the mouth into the stomach of the patient by pulling ("pulling method") or pushing ("pushing method") the guide wire.

Prior to the delivery of the PEG catheter into the stomach from the mouth of the patient, the PEG catheter is entirely enclosed with the infection preventive cover including the long sheath having at least one opening end, and the opening end of the sheath is closed in the vicinity of the position of a joint between the PEG catheter and the guide wire. The PEG catheter may be inserted into the sheath when the infection preventive cover is manufactured, or alternatively the PEG catheter may be inserted into the sheath in the performance of an operation.

The PEG catheter is delivered through the oral cavity into the stomach with the PEG catheter covered with the infection preventive cover, and the opening end of the sheath is opened in the stomach. The PEG catheter is drawn through the stomach wall and the abdomen wall into a space outside the patient together with the outer tube, while the PEG catheter is drawn through the opening end of the sheath opened. Thereafter the infection preventive cover is removed from the oral cavity into a space outside the patient. The distal end portion of the PEG catheter is left in the stomach (inclusive of a case where the distal end portion is cut off from the catheter).

In accordance with the present invention, the PEG catheter (and, in some cases, the joint section between the PEG catheter and the guide wire in dependence upon the construction of the PEG catheter) is covered outside the oral cavity with the infection preventive cover having a sheath to be delivered from the oral cavity into the stomach in the covered state. Since the opening end of the infection preventive cover is closed until the cover reaches the stomach, the PEG catheter does not directly brought into contact with the oral cavity, the larynx and the upper pharynx of the patient. The PEG catheter is therefore kept clean.

The opening end of the infection preventive cover is opened in the stomach of the patient, and the PEG catheter is withdrawn through the opening end of the cover and is drawn through a hole (wounded part of the patient) prepared in the abdominal and stomach walls into a space outside the patient. When the PEG catheter is delivered into the stomach, the catheter is kept clean, namely, is not inflected. Even when the clean PEG catheter is brought into contact with the hole (wound) in the abdominal and stomach walls, the hole (wound) is hardly inflected. Consequently, infection of the wound can be efficiently prevented.

In accordance with the present invention, the closing thread is embroidered along the circumferential edge of the opening end of the sheath in advance. The closing thread is inserted into the one end of the tightening tube, passed through the tightening tube and drawn into outside from the other end of the tightening tube. If the portion of the closing thread which is led outside from the other end of the tightening tube is pulled and the tightening tube is pushed until the one end of the tightening tube abuts against the embroidered portion, the opening end is fastened or tightened by the closing thread passing through the embroidered portion and the opening end is closed. The opening end of the sheath is kept in the closed state, when the closing thread is kept or held or maintained in the strained or tensed state, for example, by a clamping member. If the strained closing—thread is loosened, for example, the clamping member is removed or unfastened, the opening end of the sheath is naturally opened (due to the elasticity of the sheath) or becomes openable state. The operator need not be skillful with fingers to close the opening end of the sheath and to re-open the closed opening-end. The gastrostomy can be hence completed in a short period of time.

An infection preventive kit in accordance with the present invention includes a sheath having at least one opening end, a closing thread embroidered along a circumferential edge of the opening end of the sheath, a tube for tightening through which the closing thread is loosely passed, and a clamping member for keeping the opening end of the sheath being closed by the closing thread. The infection preventive kit is a combination of the sheath, the closing thread, the tightening tube and the clamping member, and is provided or supplied as the combination. Accordingly, the operator has only to cover the PEG catheter with the infection preventive cover, i.e., to insert the PEG catheter into the sheath before or in the operation of gastrostomy.

Preferably, the tightening tube is provided or supplied in the state that the tube is covered with a cover (the tube is inserted between the cover and the sheath).

The infection preventive kit is used in a method of gastrostomy in the same way as described above to prevent infection of the wound. It is possible to make it easy to open or close the opening end of the sheath by pulling the closing thread with respect to the tightening tube or loosening the strained state of the closing thread.

In one embodiment of the present invention, the clamping member is an elastic member which the portion of the closing thread led outside the tightening tube penetrates. When the closing thread is pulled in order to close the opening end of the sheath, and the clamping member is moved to a position where the clamping member abuts against the other end of the tightening tube, the closing thread cannot move any more by a frictional force between the closing thread and the elastic member and held in the strained state. The other members than the elastic member can be used as the clamping member, for example, a member having a slit formed thereon to sandwich the closing thread between portions of the member existing both sides of the slit, or clips.

The present invention further provides an infection preventive catheter kit including the infection preventive cover or the infection preventive kit. The infection preventive catheter kit comprises a percutaneous endossopic gastrostomy (PEG) catheter, a sheath, into which the PEG catheter has been inserted, having at least one opening end, a closing thread embroidered along a circumferential edge of the opening end of the sheath, a tightening tube inside of which the closing thread loosely passes through, and a clamping member for keeping a state in which the opening end of the sheath is closed by the closing thread.

Since the PEG catheter has been covered with the sheath, a work for covering the PEG catheter with the sheath can be dispensed with. The gastrostomy operation can be completed in a short period of time. Using the closing thread and the tightening tube, the opening end of the sheath can be closed and can be opened in the stomach.

The present invention further provides a percutaneous endoscopic gastrostomy (PEG) catheter, which has a top portion of conical shaped. The conical top portion is hollow and has an opening formed thereon at the top end thereof. The opening has such size that an engaging head formed at a top end of a guide wire passes therethrough, and the inside of the conical hollow top portion is larger than the opening in diameter. The hollow conical top portion is provided with an engaging piece on the inside thereof, the engaging piece allowing the bead of the guide wire which is inserted into the opening to pass therethrough and preventing the head from being pulled out.

The transversal section of the inside of the conical hollow top portion and the top opening are not limited to a circle. In a case where the transversal section of the hollow inside of the conical top portion is rectangle or other shapes, the expression that the inside of the conical hollow top portion is larger than the opening in diameter means that a side or a diagonal of the transversal section of the hollow inside of the conical top portion is larger or longer than the diameter, side or diagonal of the top opening.

There are following merits in using the above PEG catheter of the present invention. When the guide wire which is pulled through an esophagus and an oral cavity into a space outside the patient is joined with the top portion of the PEG catheter in the method of gastrostomy, the operator has only to insert the top end (head) of the guide wire into the opening formed on the conical top portion. The head formed on the top end of the guide wire enters into the hollow inside of the top portion through the top opening. The guide wire and the head are prevented from being pulled out by the engaging piece. Thus the guide wire is joined with the conical top portion of the PEG catheter. Accordingly, work for joining the guide wire with the PEG catheter is easy and time required for gastrostomy is shortened. In one embodiment, the engaging piece is disposed inside of the conical hollow top portion obliquely with respect to an axial direction of the conical hollow top portion, and the engaging piece is formed with a first slit for passing having a width larger than the head of the guide wire at an end portion of the piece which is directed to the guide wire insertion direction and a second slit for pull-out prevention having a width smaller than the head of the guide wire and being coupled with the first slit.

As described above, the first wide slit for passing which is formed on the engaging piece provided in hollow inside of the conical top portion of the PEG catheter allows the head formed on the top end of the guide wire to pass therethrough. When the guide wire is inserted into the hollow inside of the conical top portion through the top opening, the inserted head of the guide wire proceeds to through the first slit of the engaging piece (beyond the engaging piece). The guide wire portion (exclusive of the head) enters (falls down) into the narrow slit for pull-out prevention which is connected to or coupled with the wide first slit. Since the second slit is narrower than the top head of the guide wire in width, the top head is prevented from being pulled out (moving) even if the guide wire is pulled toward outside. The guide wire and the PEG catheter can be easily joined or linked and time required for gastrostomy is shortened.

BRIEF DESCRIPTION OF THE DRAWINGS

The objects and features of the present invention will become more apparent from the consideration of the following detailed description taken in conjunction with the accompanying drawings in which:

FIGS. 20A to 20D collectively show a PEG catheter kit in which FIG. 20A is a partially cut-away perspective view of a PEG catheter kit, FIG. 20B is a cross-sectional view showing a state in which a joint wire is linked with a guide wire, FIG. 20C is a cross-sectional view showing a state in which the joint is moved into a sheath, and FIG. 20D is a perspective view showing a state in which a head and a sheath are partly broken; and FIGS. 21A to 21D are diagrams showing another example of a PEG catheter kit in which FIG. 21A is a side view of the PEG catheter kit, FIG. 21B is a partially cut-away side view showing a state in which a joint is covered with a slider, FIG. 21C is an enlarged cross-sectional view of a head along line C—C, and FIG. 21D is a cross-sectional view in a state in which the head is broken.

FIG. 23 is a perspective view of an infection preventive cover according to a second embodiment;

FIGS. 36A to 36C are a partially cut-away perspective view showing a process in which a guide wire is connected to a PEG catheter, wherein FIG. 36A shows a state before connection, FIG. 36B shows a state in which the guide wire is inserted into the PEG catheter, and FIG. 36C shows the top of the guide wire is engaged with a plate;

FIGS. 37A to 37C are a partially cut-away and enlarged perspective view showing a process in which a guide wire is connected to a PEG catheter, wherein FIG. 37A shows a state before connection, FIG. 37B shows a state in which the guide wire is inserted into the PEG catheter, and FIG. 37C shows the top of the guide wire is engaged with a plate;

DESCRIPTION OF THE PREFERRED EMBODIMENTS

First Embodiment

Figure 1:
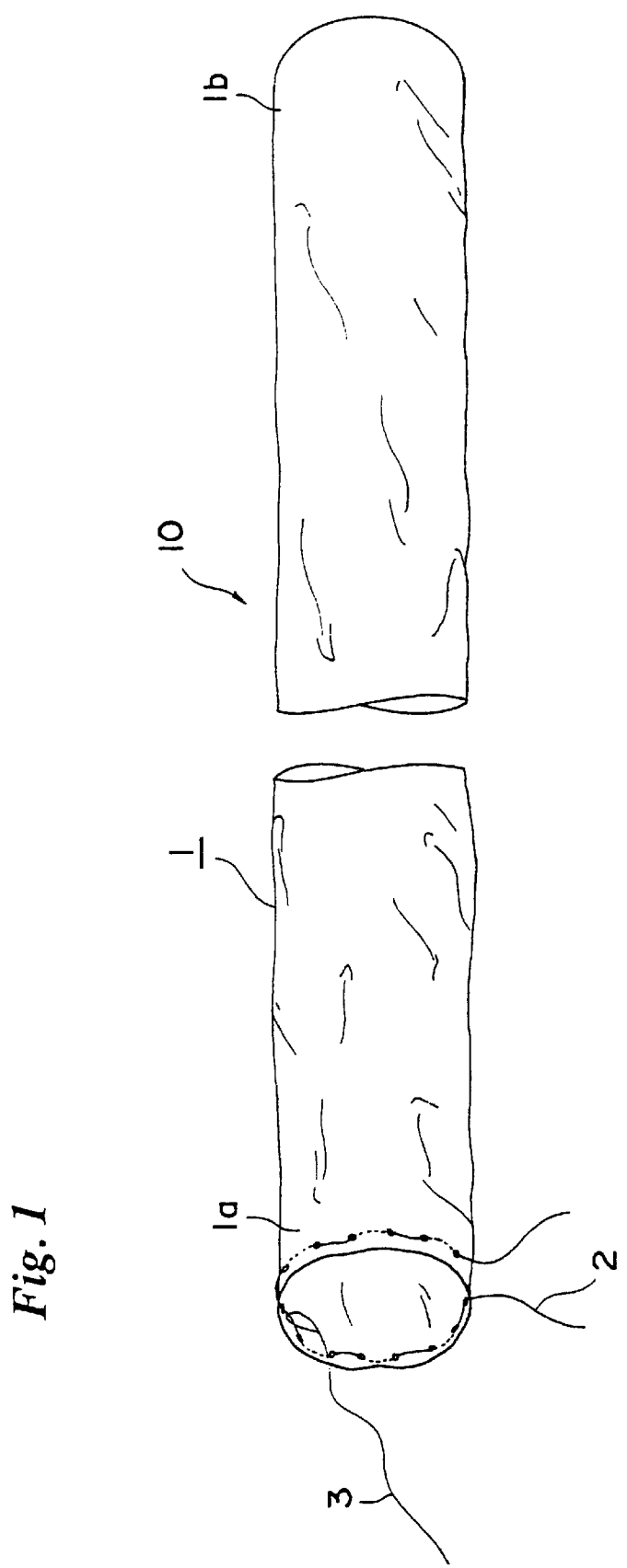
FIG. 1 is a perspective view of an infection preventive cover according to a first embodiment.

FIG. 1 shows an infection preventive cover of the first embodiment used in a percutaneous endoscopic gastrostomy (PEG).

The infection preventive cover 10 includes an elongated sheath 1 having at least one end 1a opened. The sheath 1 includes another end 1b, which may be closed, opened, or provided with a hole. The sheath 1 has a length greater than that of a gastrostomy catheter (referred to as "a PEG catheter") 12, which will be described later. The diameter of the sheath 1 is substantially equal to, or greater than that of a dome 13 connected to an end edge of the catheter 12.

When the sheath 1 is made of a elastic or expansive material, the diameter thereof may be slightly smaller than that of the dome 13. In either case, it is only required that the PEG catheter 12 including the dome 13 passes through the sheath 1. It is desirable that a lubricant such as a lubricant jerry is applied on an inner surface of the sheath 1.

The sheath 1 is manufactured with a thin, airtight, waterproof, flexible and strong material such as vinyl or a rubber. Favorably, the sheath 1 includes a possibly thin wall and has elasticity (especially in a circumferential direction). The sheath 1 is depicted in swollen out form to show a cylindrical and hollow body for easily understanding.

Figure 16:
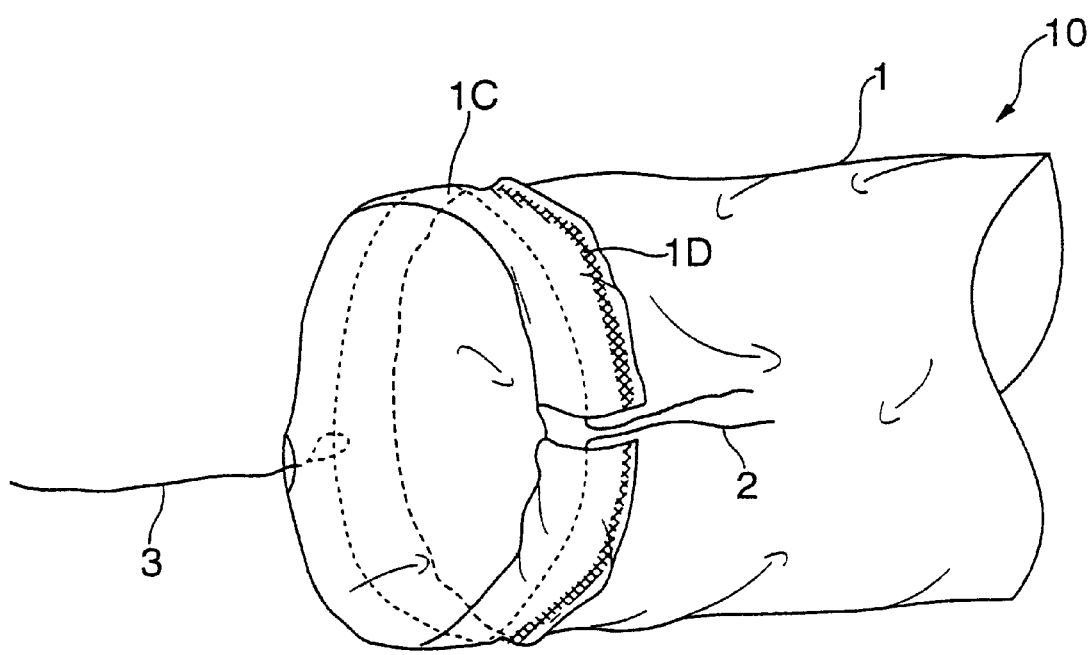
FIG. 16 is an enlarged perspective view showing another example in which a ligature is provided to an opening end of an infection preventive cover.

A circumferential periphery of the opening end 1a of the sheath 1 is embroidered with a ligature (a binding thread) 2 along the circumference, i.e., is continuously stitched from an outer side to an inner side and vice-versa with an appropriate interval (this state is referred to as "embroidered"). In addition to this state, the expression "embroidered with the ligature" also includes a state in which, as shown in FIG. 16, the circumferential periphery portion 1C of the opening end of the sheath 1 is folded back outside (or inside) and the folded-back portion 1C is melted (or welded or adhered) at its edge to the sheath 1 (the adhered portion is indicated by a reference numeral 1D) to form a bag, a path or guide along the edge of the opening end of the sheath 1, and the ligature 2 is passed therethrough. Both ends of the ligature 2 are outwardly led from the circumferential peripheral of the sheath 1 at positions near to each other. The ligature 2 is bound with one end of a cutting wire (thread) 3, which is guided out of the sheath 1. Favorably, the one end of the cutting wire 3 is coupled with the ligature 2 within the sheath 1. Furthermore, the cutting wire 3 is favorably coupled with the ligature 2 at a position most apart from the positions at which the ends of the ligature 2 are outwardly lead from the sheath 1 (i.e., the position of the cutting wire 3 and the positions of the ends of the ligature 2 are substantially opposing to each other on the sheath 1). In FIG. 16, the cutting wire 3 is led to outside through a hole formed on the bag, path or guide.

The cutting wire 3 is stronger than the ligature 2. For example, a thin metallic thread is employed as the cutting wire and a silk thread is utilized as the ligature 2. For the cutting wire 3 and the ligature 2, there may be employed threads respectively made of linen, cotton, polyester, polyethylene, and any other vegetable or chemical fiber.

Referring now to FIGS. 2 to 13, description will be given in detail of a usage method and a role of the infection preventive cover 10 configured above in relation to the PEG method. In this example, a method called "pull method (technique)" will be described. The PEG method is performed in general by an operator, an endoscopist and one or two nurses.

Figure 2:
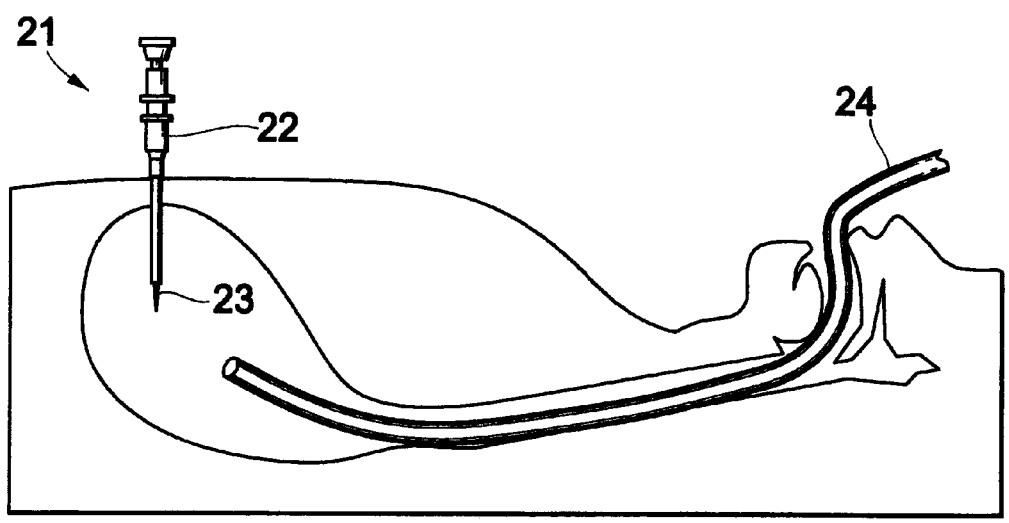
FIG. 2 is a cross-sectional view schematically showing an upper half of a body of a patient in which a endoscope is inserted in the body in a PEG process.

An endoscope 24 is inserted from a mouth of a patient in a supine position into her or his stomach. Air is fed through the endoscope 24 into the stomach of the patient to expand the stomach to resultantly tightly fix the stomach wall onto a peritoneum of the patient. A puncturing part is determined and its peripheral is completely disinfected. After the periphery is locally anesthetized, about one centimeter of skin is incised in the puncturing part and then a needle 21 with an outer tube is pierced thereinto (FIG. 2).

The needle 21 includes an outer tube (pipe) 22 of a cylindrical contour and a needle (inner tube 23) having a sharp end. The outer tube 22 is hallow. With the needle 23 completely installed in the external tube 22, the sharp end of the needle 23 is projected from an end of the outer tube 22. The sharp end of the needle 23 thrusts into the abdomen wall, the peritoneum and the stomach wall, and the outer tube 22 also passes through the abdomen wall, the peritoneum and the stomach wall.

Figure 3:
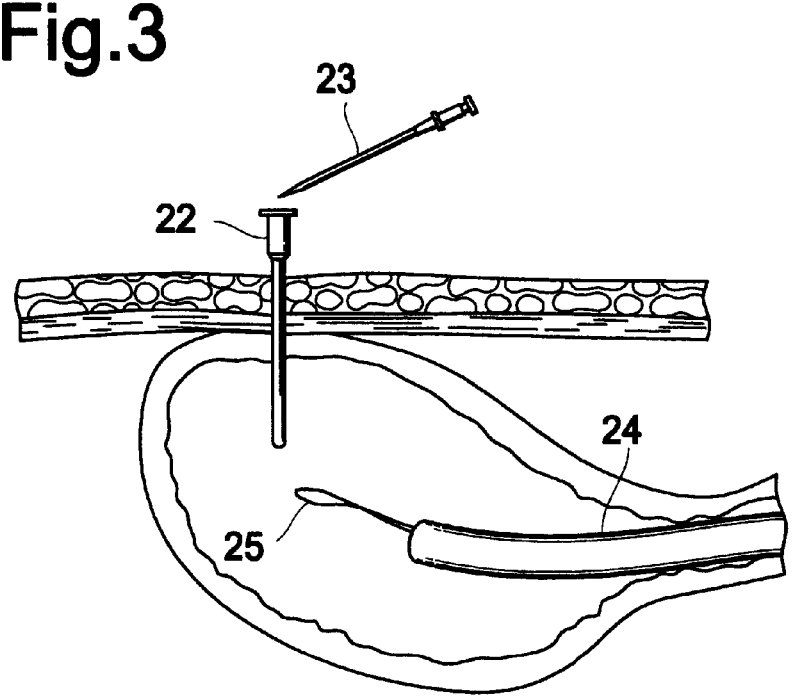
FIG. 3 is a cross-sectional view schematically showing an enlarged part of a stomach of a patient in which a endoscope is inserted in the body in a PEG process.

The needle 23 is removed from the outer tube 22. The outer tube 22 is kept pierced ranging from the abdomen wall to the stomach wall. An end of a snare forceps 25 is drawn from an end of the endoscope 24 to be exposed in the stomach (FIG. 3).

Figure 4:
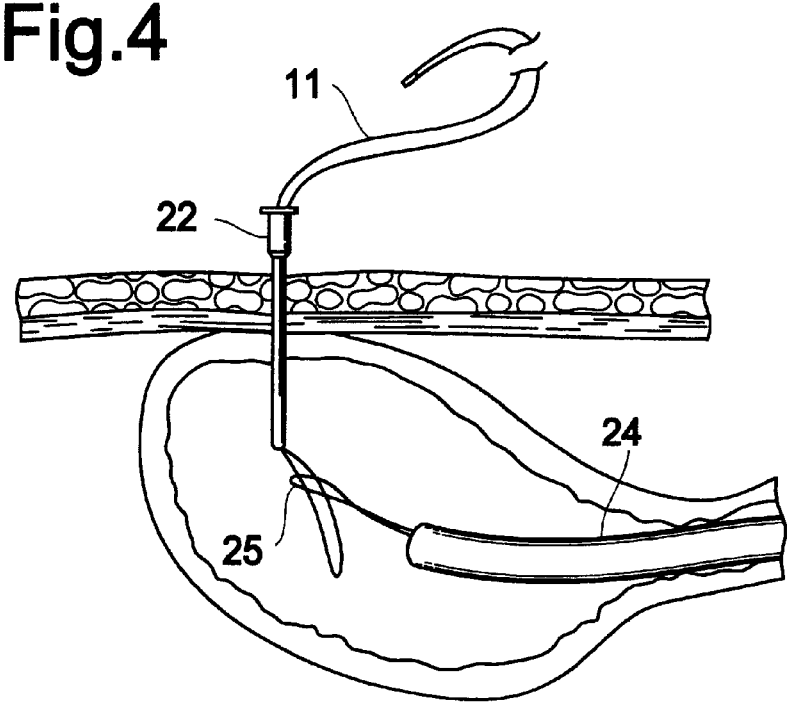
FIG. 4 is a cross-sectional view schematically showing a part of a stomach of a patient in which a guide wire is inserted into the stomach in a PEG process.

A guide wire 11 is passed through the outer tube 22 to be inserted into the stomach (FIG. 4).

Figure 5:
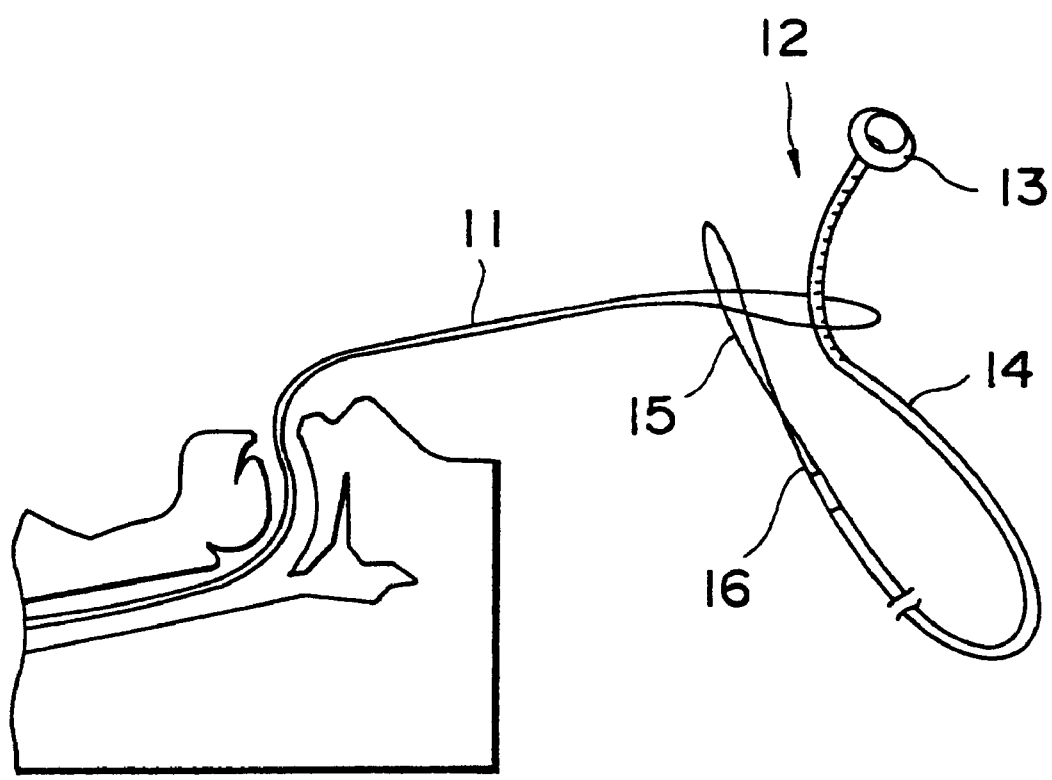
FIG. 5 is a perspective view showing a linkage between a guide wire and a joint wire in a PEG process.

An end of the guide wire 11 fed into the stomach is grasped by the snare forceps 25. The guide wire 11 held by the snare forceps 25 is withdrawn out of the oral cavity of the patient together with the endoscope 24. After the guide wire 11 is sufficiently drawn out of the oral cavity, the snare forceps 25 is released from the guide wire 11. The guide wire 11 thus drawn out of the oral cavity is coupled with a joint wire 15 of the PEG catheter 12 (FIG. 5).

The PEG catheter 12 includes a PEG tube 14 which has one end at which a dome 13 is integrally coupled with or connected to and which has another end tapered in a cone shape (this section is called a taper section 16). The taper section 16 is linked with the joint wire 15. A end of the joint wire 11 in a doubled form is entangled with the joint wire 15 such that the guide wire 11 is coupled with the joint wire 15 (the section of the coupling between the guide wire 11 and the joint wire 15 is called a joint 17; reference is also to be made to FIG. 12).

Figure 6:
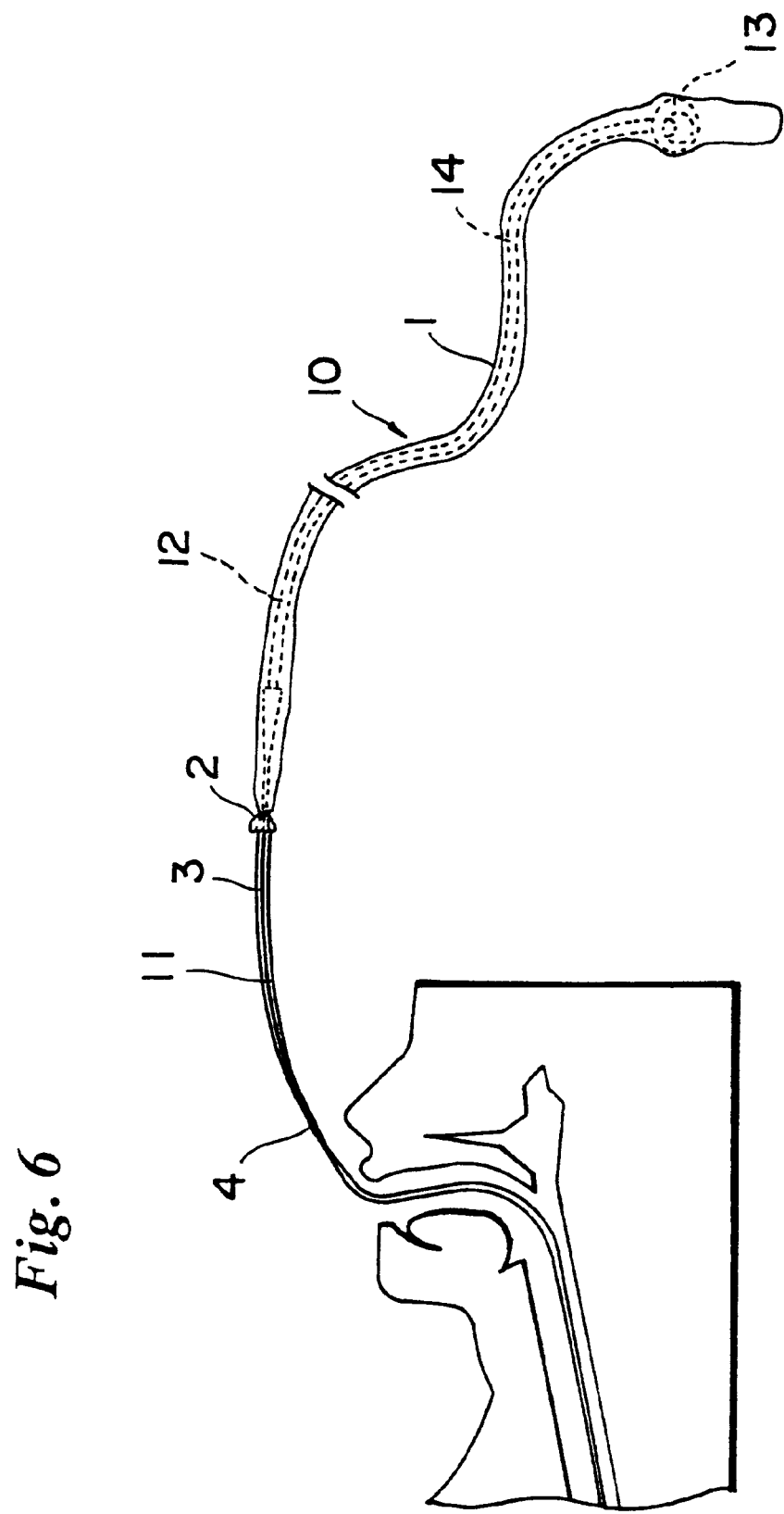
FIG. 6 is a cross-sectional diagram schematically showing a portion ranging from a head to an upper pharynx of a patient in a PEG process.

Thereafter, a portion of the PEG catheter 12 ranging from the dome 13 to the joint 17 is inserted into the sheath 1 of the infection preventive cover 10 and then both ends of the ligature 2 are tightly fastened (FIG. 6).

Figure 12:
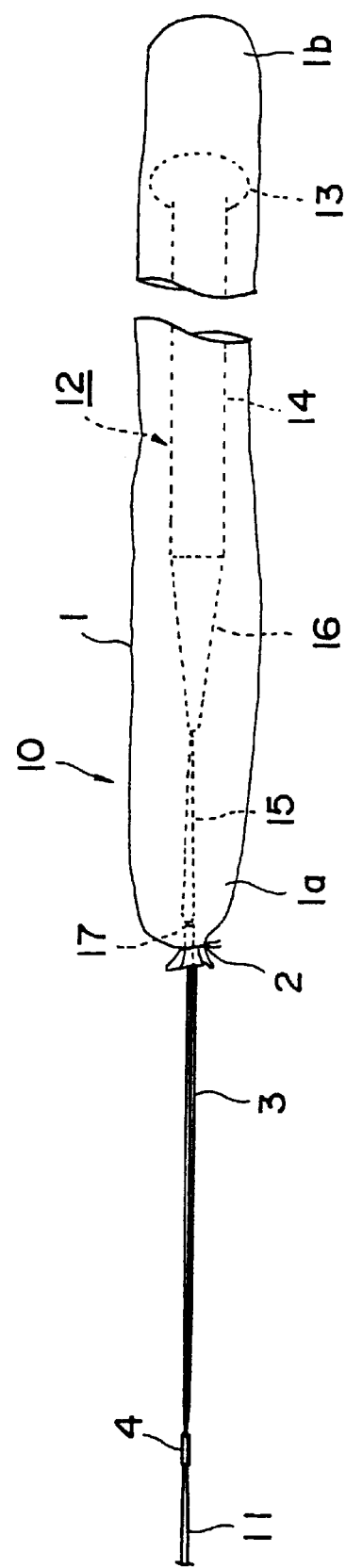
FIG. 12 is a perspective view showing a state in which a PEG catheter is covered with an infection preventive cover.

FIG. 12 shows in an enlarged diagram a state in which the opening end 1a of the sheath 1 of the infection preventive cover 10 is tied up by the ligature 2. The ligature 2 is tightly bound, for example, in a surgical knot at a position slightly shifted from the joint 17 in the sheath 1 toward the side of the guide wire 11. As a result, the opening end 1a of the sheath 1 is fixedly tightened to be closed (the opening end 1a thus ligatured of the sheath 1 will be referred to as a ligatured end herebelow). An unnecessary section of each end of the ligature 2 is cut away.

Figure 13:
FIG. 13 is an enlarged plan view schematically showing a state in which a cutting wire is fixed onto a guide wire.

The cutting wire 3 is extended along the guide wire 11 and an end of the cutting wire 3 is fixed onto the guide wire 11 by a fixing unit such as a tape 4. FIG. 13 schematically shows an enlarged image of the end of the cutting wire 3 fixed onto the guide wire 11. The fixed section (tape 4) of the cutting wire 3 must be of a small size to pass through the outer tube 22.

Figure 14:
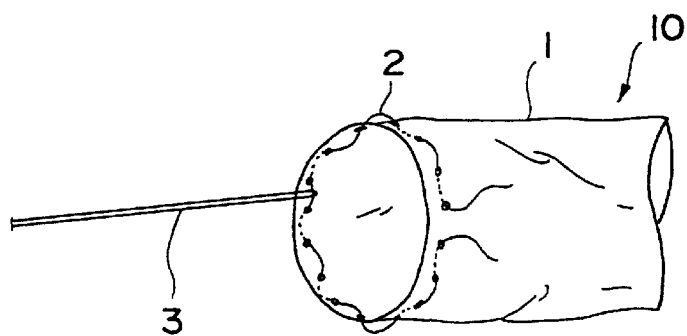
FIG. 14 is a perspective view showing another example of the joint between a ligature at an opening end of an infection preventive cover and a cutting wire.

As can be seen from FIG. 14, it may also be possible that the ligature 2 is engaged with or hooked by the cutting wire 3, and the cutting wire 3 is bent (without being bound), the cutting wire 3 in the double form is arranged along the guide wire 11, and then both ends of the cutting wire 3 are fixed onto the guide wire 11.

Figure 7:
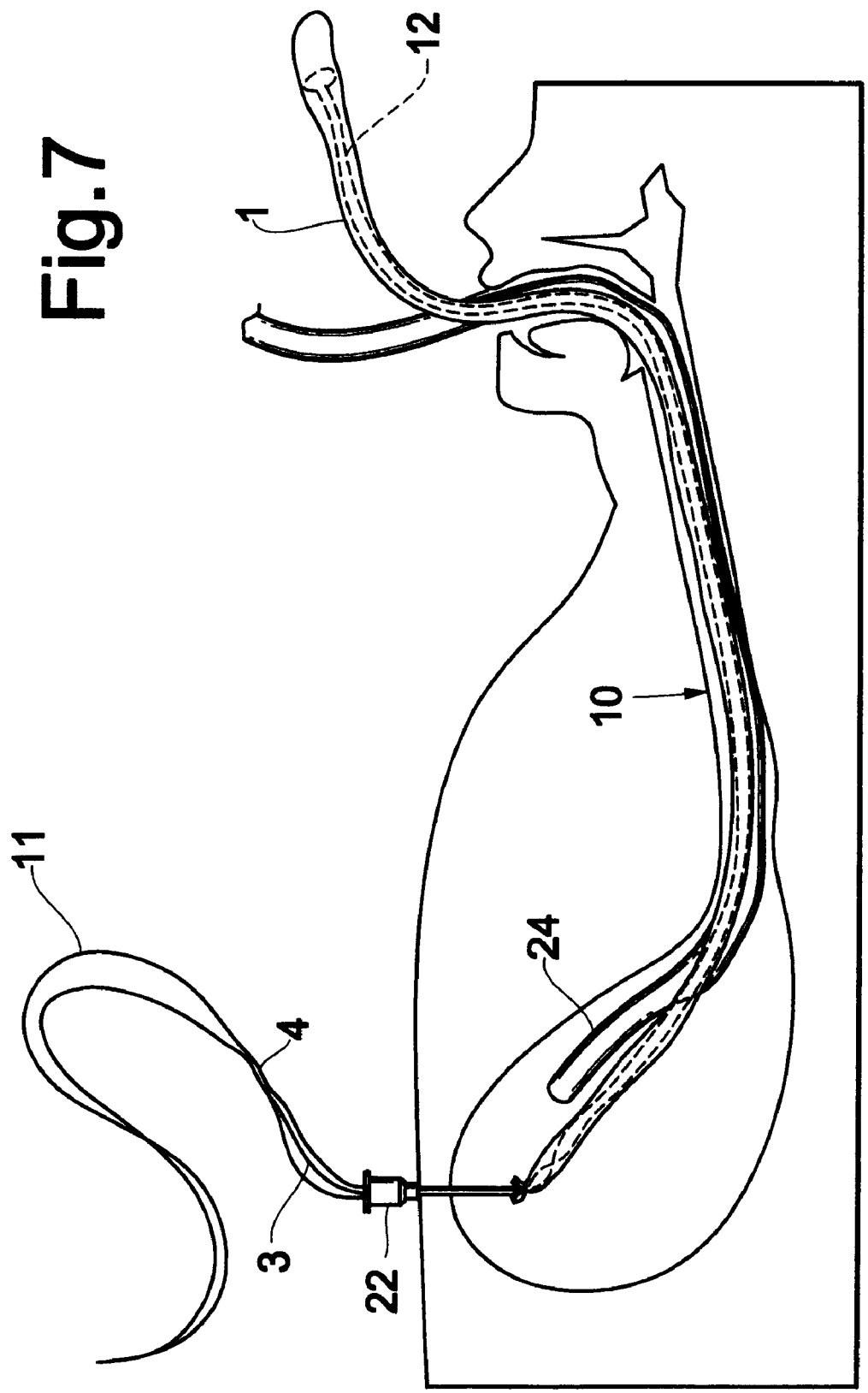
FIG. 7 is a cross-sectional view schematically showing an upper half of a body of a patient in which a PEG catheter covered with an infection preventive cover is pulled in a PEG process.

The end of the guide wire 11 drawn through the outer tube 22 into a space outside the body of the patient is pulled. This causes the PEG catheter 12 coupled with the guide wire 11 to be delivered through the oral cavity, the upper pharynx and the larynx into the stomach with the catheter 12 covered with the sheath 1 (FIG. 7).

At the same time, the endoscope 24 is again inserted through the oral cavity into the stomach. By inserting the endoscope 24 along the PEG catheter, it is possible to smoothly move the endoscope 24 into the stomach of the patient.

Figure 8:
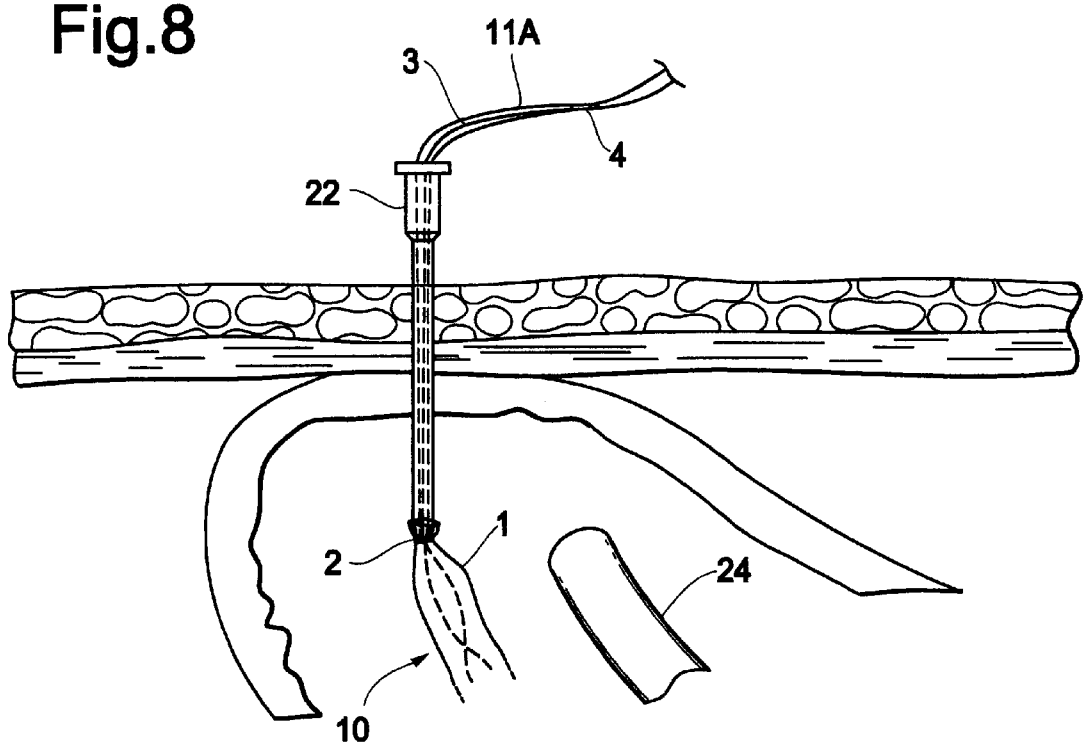
FIG. 8 is a cross-sectional view schematically showing an enlarged part of a stomach of a patient in which a PEG catheter covered with an infection preventive cover is pulled in a PEG process.

The cutting wire 3 fixed onto the guide wire 11 is also withdrawn together with the guide wire 11 through the outer tube 22 out of the abdomen wall. When the guide wire 11 is further drawn, the ligatured end of the sheath 1 abuts on an end of the outer tube 22 (FIG. 8). It is favorable to confirm this event, i.e., the ligatured end of the sheath 1 abuts on an end of the outer tube 22 by the endoscope 24. In this state, the PEG catheter 12 and another end of the sheath 1 are still outside the mouth of the patient (FIG. 7). It may also be favorable to confirm by a hand that the ligatured end of the sheath 1 abuts on the end of the outer tube 22. It may thereafter be possible to insert the endoscope 24 into the stomach. The second insertion of the endoscope 24 may be avoided.

Figure 9:
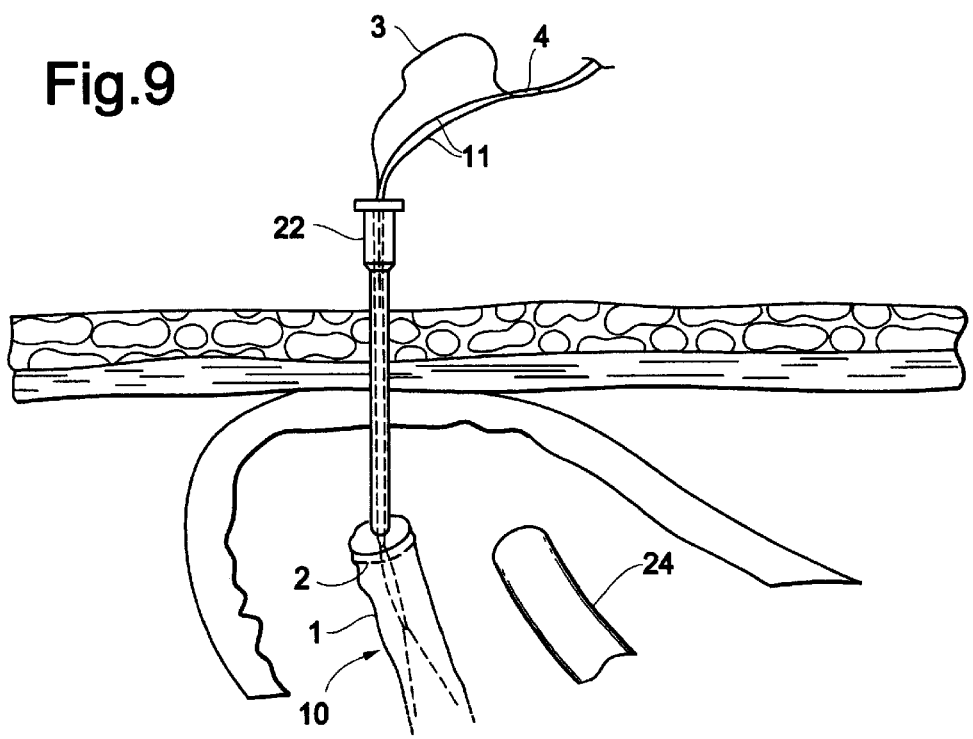
FIG. 9 is a cross-sectional view schematically showing an enlarged part of a stomach of a patient in which an opening end of a sheath is opened in a PEG process.

The cutting wire 3 outside the patient is then drawn (pulled). In this situation, it is favorable that the endoscopist holds the sections of the PEG catheter 12 and the sheath 1 outside the mouth of the patient by slightly pulling these sections. Since the cutting wire 3 is stronger than the ligature 2, the ligature 2 is cut by the cutting wire 3 in the stomach. Resultantly, the ligatured state of the sheath 1 by the ligature 2 is released and the opening end of the sheath 1 is opened (FIG. 9). If necessary, a section of the ligature 2 is fixed onto the sheath 1 by an adhesive or the like such that the ligature 2 thus cut off does not fall into the stomach.

It is desirable that the opening end 1a of the sheath 1 is beforehand prepared to easily open outwardly, for example, by bending the opening end 1a several times or by giving nature to open. With this preparation, it is guaranteed that the sheath 1 opens when the ligature 2 is cut off.

Figure 15:
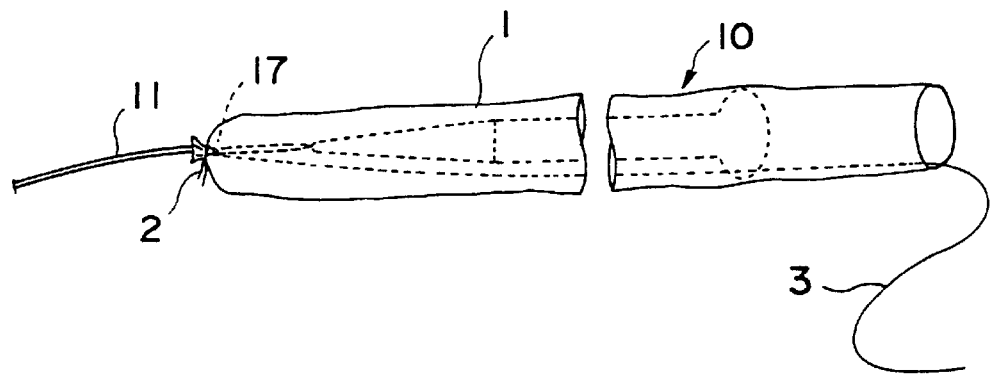
FIG. 15 is a side view showing a state of a PEG catheter covered with an infection preventive cover in another example in which a cutting wire bound on a ligature at an opening end of an infection preventive cover is drawn outwardly.

It may also be possible that the cutting wire 3 is outwardly withdrawn on the side of the oral cavity of the patient to thereby cut off the ligature 2. In this case, as shown in FIG. 15, an end of the cutting wire 3 is linked with the ligature 2 in the sheath 1 and another end thereof is passed through the sheath 1 to be outwardly fed through an opening (or a hole) on another end of the sheath. When the cutting wire 3 is pulled on the side of the oral cavity, the ligature 2 is cut off. If a section of the cutting wire 3 near the ligatured end is adhered, welded or melted onto an inside of the sheath 1, the sheath 1 is also broken up to an intermediate part thereof to provide a larger opening when the cutting wire 3 is pulled and the ligature 2 is accordingly cut off.

Figure 10:
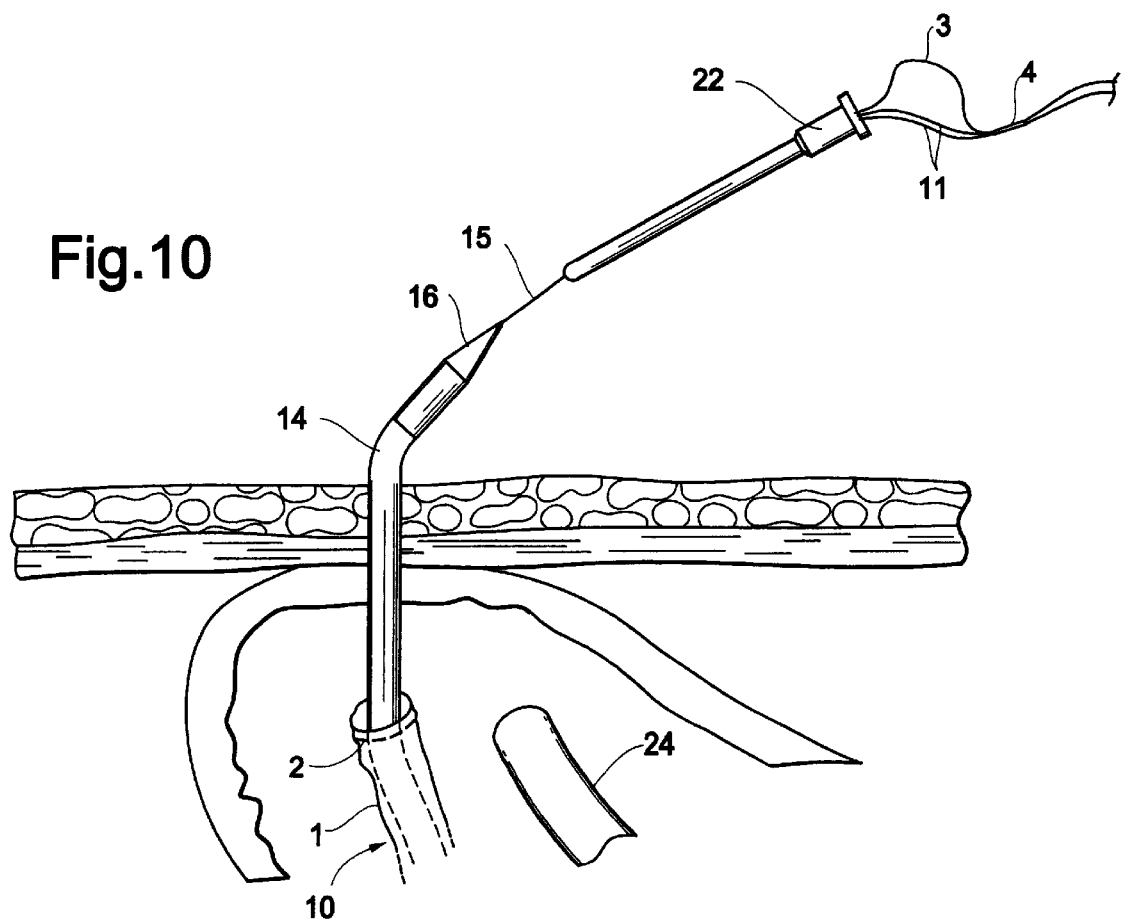
FIG. 10 is a cross-sectional view schematically showing an enlarged part of a stomach of a patient in which a PEG catheter is drawn out of a body in a PEG process.

While the outer tube 22 is being drawn through the stomach and abdomen walls, the guide wire 11 is further withdrawn outwardly. The joint wire 15, the taper section 16, and the PEG tube 14 are delivered through the stomach wall and the abdomen wall into a space outside the patient body (FIG. 10).

When the PEG catheter 12 is being drawn toward the outside of the patient body, the endoscopist holds by a hand the end 1b of the sheath 1 outside the mouth of the patient such that the sheath 1 is not fed into the patient body.

Figure 11:
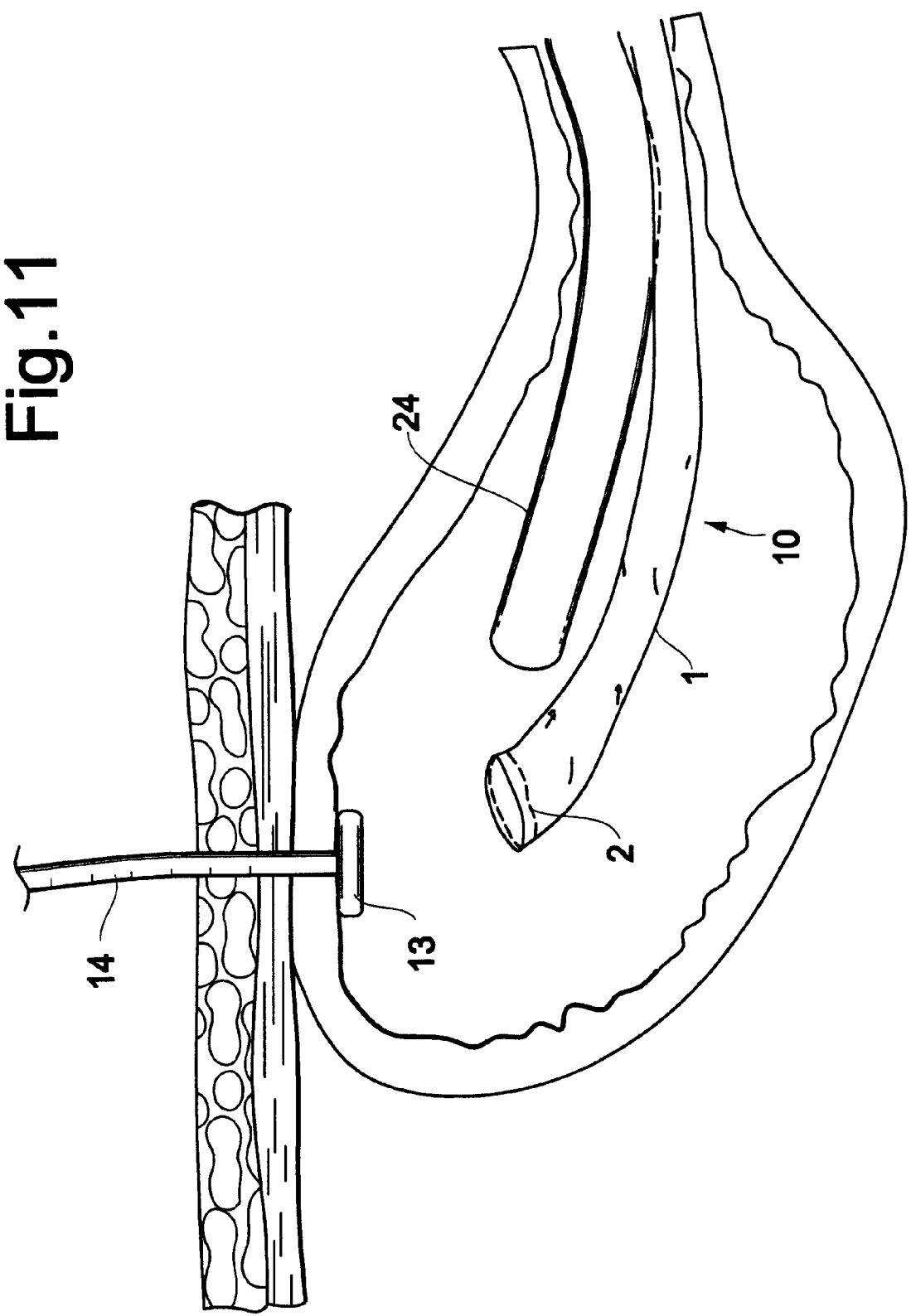
FIG. 11 is a cross-sectional view schematically showing a part of a stomach of a patient in which a dome at an end of a PEG catheter abuts on a stomach wall in a PEG process.

Finally, the dome 13 appears from the opening end of the sheath 1 and abuts on the stomach wall (FIG. 11). If necessary, this condition that the dome 13 abuts on the stomach wall is confirmed by the endoscope 24. The sheath 1 is removed from the mouth of the patient into a space outside the patient.

The PEG tube 14 thus withdrawn is cut at an appropriate point to have a necessary length, and the cut-off end is connected with an adapter to supply a medicine for nutrition. The PEG tube is attached onto the body of the patient with an appropriate fixing unit (means), thereby completing the operation of the PEG method.

Outer surfaces of the guide wire 11 and the sheath 1 having passed through the larynx, the upper pharynx and the oral cavity are infected by bacteria on the oral cavity, the upper pharynx and the larynx. However, since the guide wire 11 is drawn through the outer tube 22 into a space outside the patient body, it hardly occurs that the wound (hole) in the stomach and abdomen walls is infected by the guide wire 11. Furthermore, the joint 17 between the guide wire 11 and the joint wire 15, the joint wire 15, the taper section 16, the PEG tube 14 and the dome 13 are each covered with the sheath 1 to be fed, in this state, through the oral cavity, the upper pharynx and the larynx into the stomach to be then withdrawn from the sheath 1 in the stomach. Even when the joint 17, the joint wire 15, the taper section 16 and the PEG tube 14 are brought into contact with the wound when they are drawn to a space outside the patient, there is almost no chance that the wound is contaminated by bacteria. The sheath 1 of which outer surfaces are infected are removed through the mouth of the patient. It does not occur that the wound is infected by the infection preventive cover 10. In consequence, the infection of the wound can be advantageously prevented.

Also in the "push" method, it is possible to effectively prevent infection of the wound by pushing the PEG catheter 12 covered with the infection preventive cover 10 into the stomach.

Figure 17:
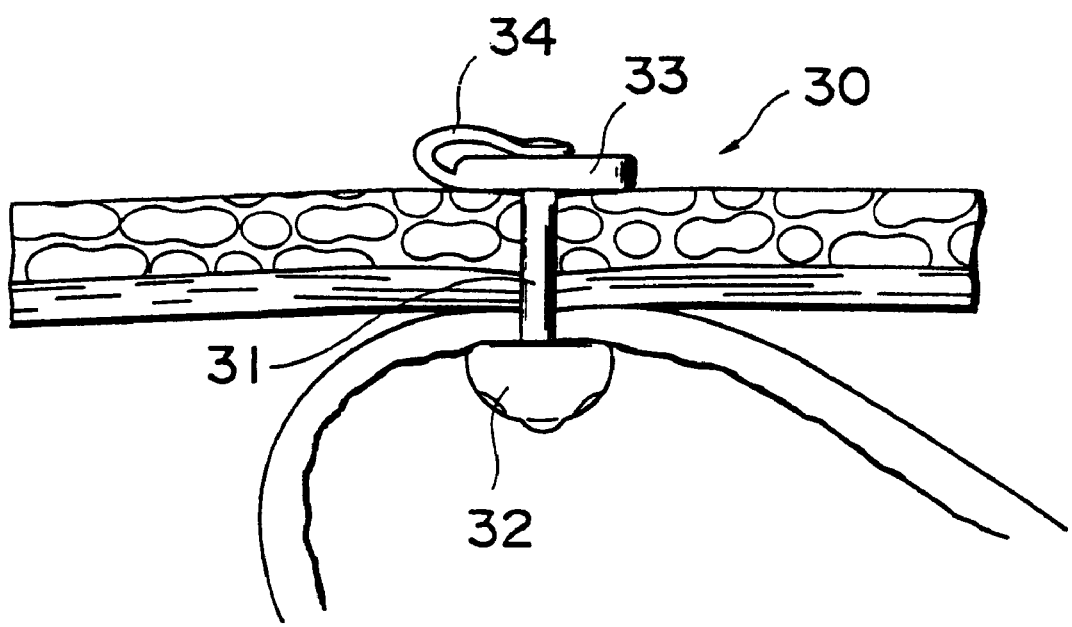
FIG. 17 is a cross-sectional view schematically showing an enlarged part of a stomach of a patient in a PEG process corresponding to FIG. 11 in which a one-step button is used.

FIG. 17 partly shows a PEG catheter (PEG tube) of a button type, the button being called one-step button. The button 30 is attached onto a tip end of a PEG tube of the PEG catheter. When the PEG tube is sufficiently drawn from the stomach into an external space of the body (corresponding to the state of FIG. 11), the button 30 is separated from the PEG tube. The one-step button 30 includes a shaft 31; a dome 32 including a counterflow preventive valve and integrally connected to an end of the shaft 31, the dome 32 being kept remained in the stomach; a stopper 33 formed integral with the shaft 31, the stopper 32 abuting on the outside of the abdomen wall; and a cap 34 linked to the stopper 33 to seal a hallow section of the shaft 11. The infection preventive cover 10 can be applied also to the button-type PEG catheter including the one-step button. It is also to be understood that the infection preventive cover 10 is applicable to PEG catheters in another configuration.

FIGS. 18A, 18B, 19A, and 19B show further examples of the ligature at the opening end of the infection preventive cover. In these diagrams, the same components as those of FIG. 1 are assigned with the same reference numerals and duplicated description thereof will be avoided.

Figure 18A:
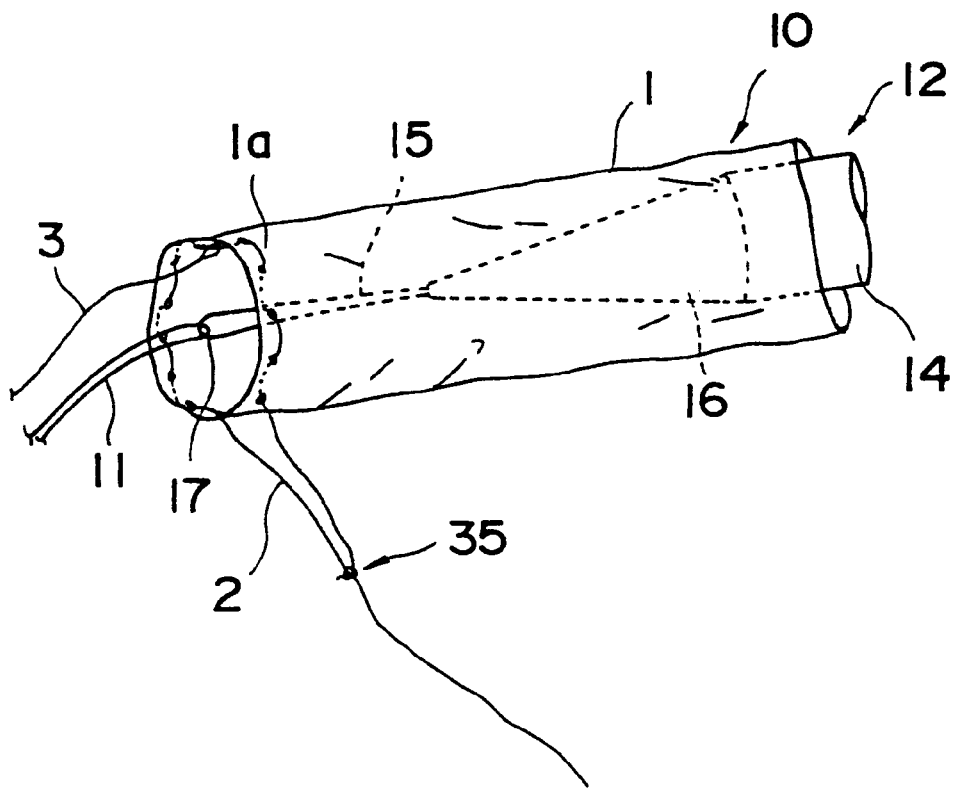
FIGS. 18A and 18B are perspective views showing another example of the ligaturing operation of an opening end of an inflection preventive cover.
Figure 18B:
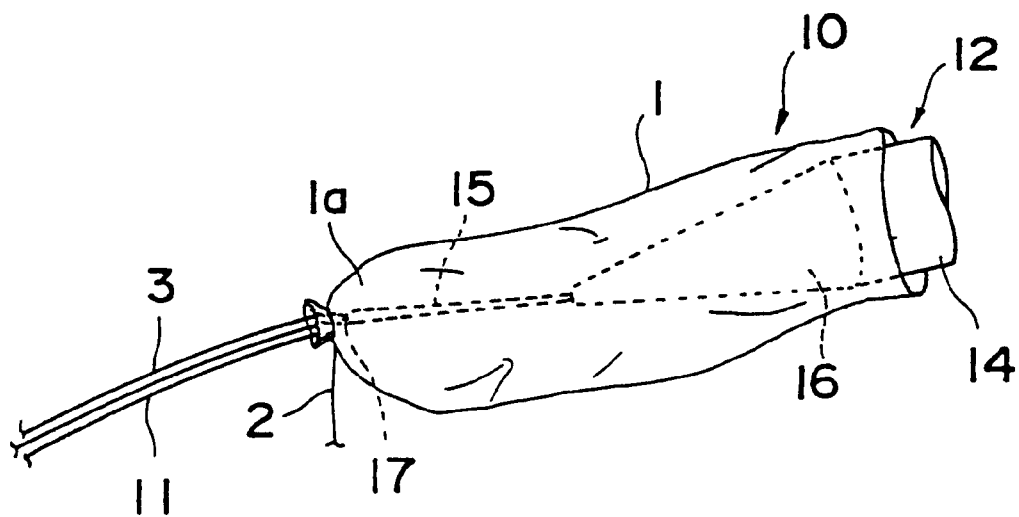

Referring to FIGS. 18A and 18B, the circumferential periphery of the opening end 1a of the sheath 1 is beforehand embroidered with the ligature 2. At an intermediate point of an end section of the ligature 2, another end thereof is fastened by a roller knot 35 (FIG. 17A). The ligature 2 is coupled with the cutting wire 3. The operator connect the guide wire 11 to the joint wire 15, covers the PEG catheter 12 with the sheath 1, and then pulls the one end of the ligature 2. The opening end 1a of the sheath 1 can be quite simply tightened (FIG. 17B). An unnecessary end section of the ligature 2 is to be cut away.

Figure 19A:
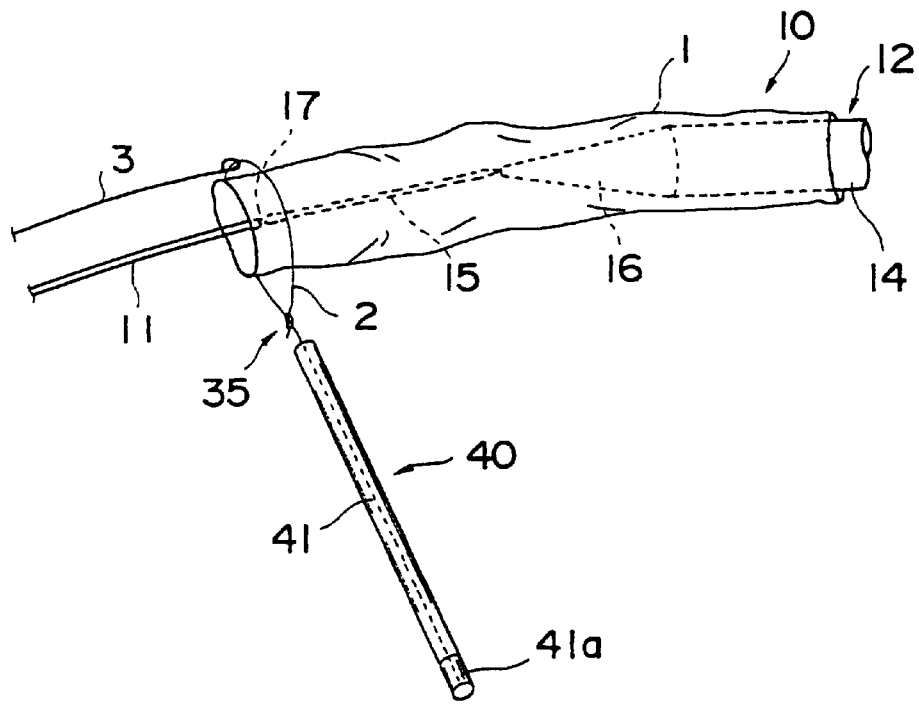
FIGS. 19A and 19B are perspective views showing further another example of the ligaturing operation of an opening end of an inflection preventive cover.
Figure 19B:
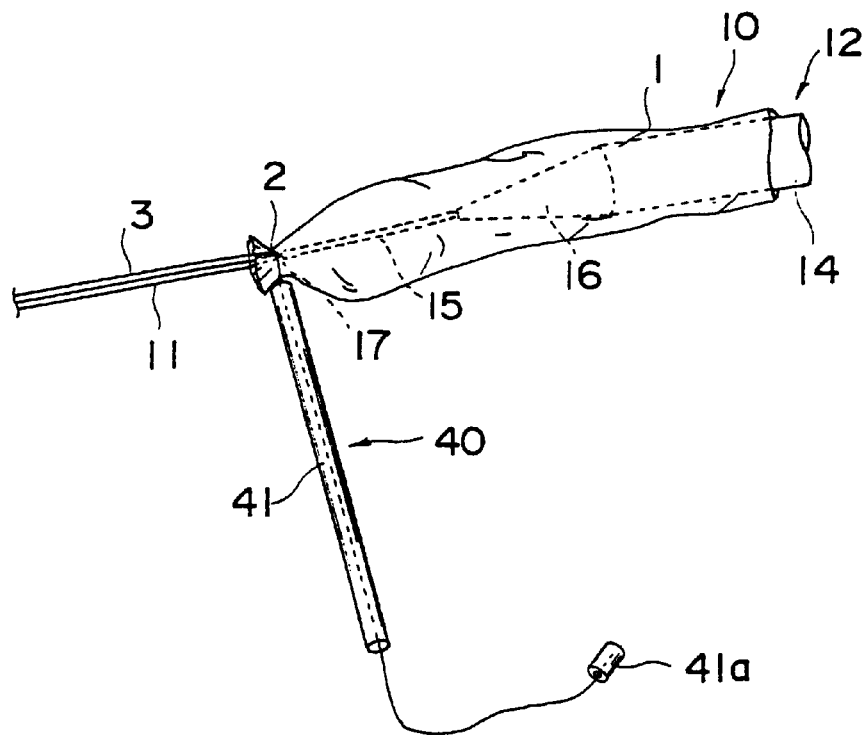

In FIGS. 19A and 19B, a ligaturing unit 40 is employed. The ligaturing unit 40 includes a ligature 2 and a tightening rod 41. In the tightening rod 41, a hole is provided along a longitudinal direction thereof. The tightening rod 41 includes a cut-away groove at an end portion thereof. The end portion of the rod 41 up to the cut-away groove is indicated by a reference numeral 41a. The ligature 2 is formed in a loop and an end section thereof is passed through the hole of the tightening rod 41 to be fixedly attached to the end portion 41a. Another end of the ligature 2 is fastened at an intermediate point of the ligature 2 by a roller knot 35. The loop of the ligature 2 is linked with the cutting wire 3.

The operator puts the sheath 1 on the PEG catheter 12 coupled with the guide wire 11, passes the PEG catheter 11 and the sheath 1 through the loop of the ligature 2, and places the loop section of the ligature 2 at a position of the sheath 1, the position being slightly apart from the opening end 1*a* (FIG. 19A). The operator bends or cuts away the end portion 41*a* of the tightening rod 41 and pulls the end portion 41*a*. The loop of the ligature 2 is tightened to close the opening circumferential periphery of the sheath 1 and the closed state is kept retained (FIG. 19B). An unnecessary part of the ligature 2 is cut away. It may naturally be possible that the opening circumferential periphery of the sheath 1 is embroidered with the ligature 2.

A PEG catheter kit can be provided. The PEG catheter kit includes a combination of a PEG catheter and the above mentioned infection preventive cover, that is, a PEG catheter covered with the infection preventive cover. A work for inserting a PEG catheter into a sheath of the infection preventive cover can be dispensed with.

Figure 20A:
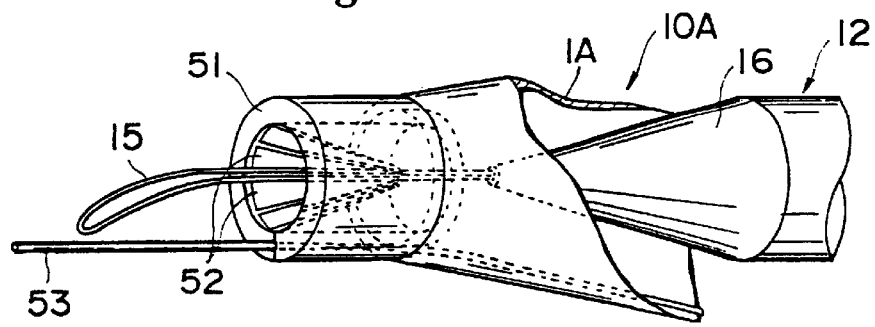
Figure 20B:
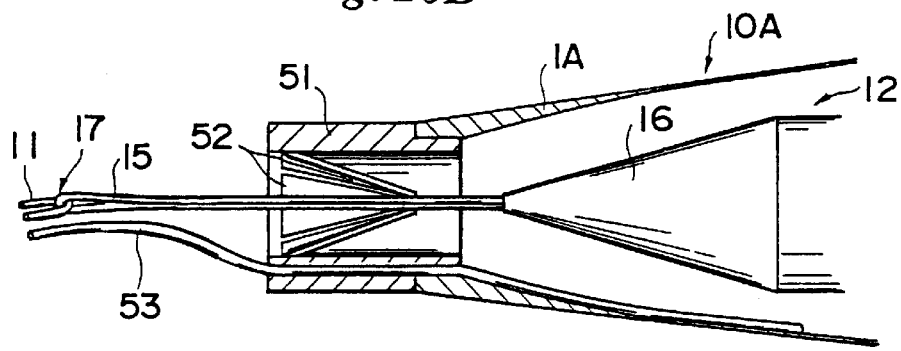
Figure 20C:
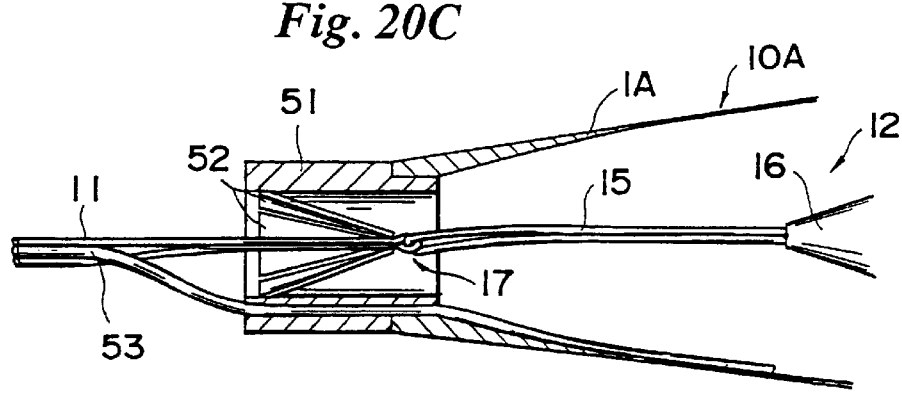
Figure 20D:
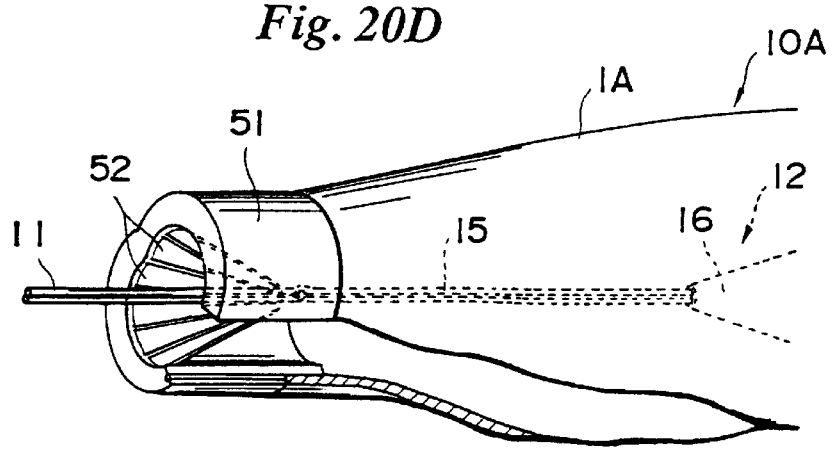

FIGS. 20A and 20D show another PEG catheter kit in which a PEG catheter and an infection preventive cover are beforehand combined.

Referring particularly to FIGS. 20A and 20B, the infection preventive cover 10A includes a head 51 and a sheath 1A.

The head 51 has a cylindrical contour and includes in its hole section a plurality of movement preventive pieces 52. The sheath 1A is fabricated in a tapered form and a tapered edge section thereof has a slightly thicker wall. Naturally, the sheath 1A may be of a uniform wall thickness. The head 51 includes a step section at which the tapered end section of the sheath 1A is fixed (welded or adhered).

The PEG catheter 12 is beforehand installed in the sheath 1A and the joint wire 15 of the catheter 12 is outwardly guided through the hole of the head 51. The movement preventive pieces 52 of the head 51 are constructed to be aligned inwardly from the end edge section of the head 51 toward the sheath 1A.

The head 51 is longitudinally cut off at a position thereof to form two junction surfaces, between which a breaking wire 53 is inserted. In this state, the junction surfaces of the head 51 is adhered or melted to be closed, sandwiching the breaking wire 53. One end section of the breaking wire 53 extends along an inner surface of the sheath 1A up to an intermediate point thereof and is adhered or melted on the inner surface of the sheath 1A. Another end section of the breaking wire 53 is lead to the outside of the sheath 1A and the head 51. It may also be possible that the section of the sheath 1A in which the breaking wire 53 is adhered or melted may also be cut off such that the cut-off section is thereafter adhered or melted together with the breaking wire 53.

As in the embodiment described above, the guide wire 11 is drawn out of the mouth of the patient and then is coupled with the joint wire 15 (FIG. 20B).

The head 51 is moved along the joint wire 15 to move the joint 17 into the sheath 1A. The joint 17 is brought into contact with ends of the movement preventive pieces 52 and hence the head 51 is prevented from moving in a direction of the joint wire 15. The breaking wire 53 is aligned with the guide wire 11 and an end section thereof is fixed on the guide wire 11 by a fixing tape or the like in almost the same way as for the cutting wire 3 shown in FIG. 13 (FIG. 20C).

By drawing the guide wire 11 through the outer tube 22 pierced through the wall of the abdomen of the patient, the PEG catheter 12 is delivered together with the infection preventive cover 10A through the mouth, the upper pharynx, the larynx and the esophagus to the stomach. When the head 51 abuts on an inner end of the outer tube 22, the breaking wire 53 which is exposed outside together with the guide wire 11 are pulled. Part of the head 51 and part of the sheath 1A are resultantly broken (FIG. 20D).

In this state, while continuously holding the end edge section of the sheath 1A outside the mouth of the patient, the operator draws the PEG catheter 12 together with the outer tube 22 out of the abdomen of the patient.

FIGS. 21A to 21D still show another example of a PEG catheter kit.

The infection preventive cover 10B includes a head 61 and a sheath 1B. The head 61 is fixed on a tip end of the sheath 1B and a breaking wire 53 is arranged as described in the embodiment above.

On an inner circumferential surface of the head 61 having a cylindrical shape, two guide grooves (dovetail grooves) 64 are formed, the grooves opposing each other. On each guide groove 64 is engaged a slider (dovetail) 65 to move in an axial direction of the head 61 (FIG. 21C). The slider 65 includes an end section on the side of the sheath 1B, the end section including a stopper 66. At an intermediate section of the slider 65, there is formed a cut-away section 68 to form a section serving as a stopper 68. On an inner surface of a tip end section of the slider 65, there is formed a depression 67.

Figure 21A:
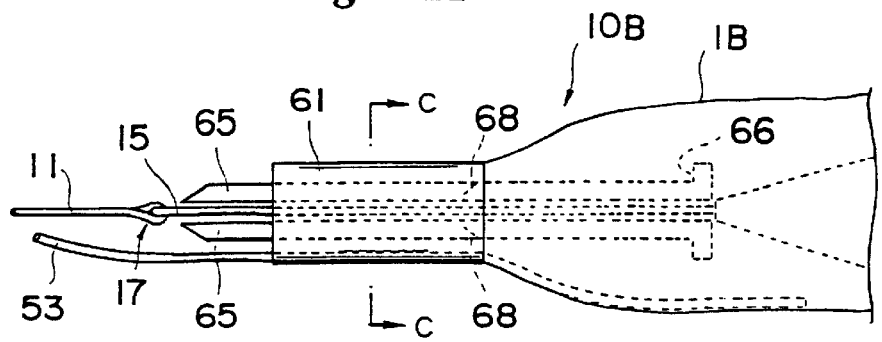
Figure 21B:
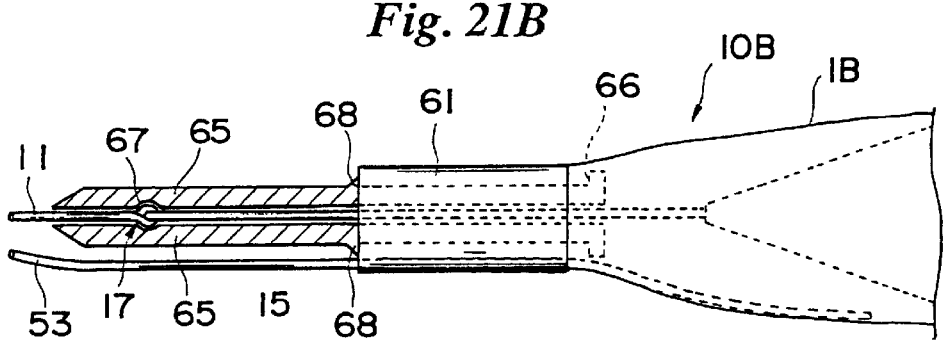
Figure 21C:
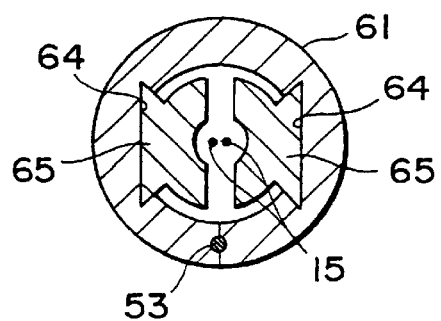

When the slider 65 is pulled outwardly, the joint 17 engages in the depression 67 of the slider 65 and the cut-away section of the slider 65 is brought into contact with the outer end section of the head 61 to function as the stopper 68 (FIG. 21B).

Figure 21D:
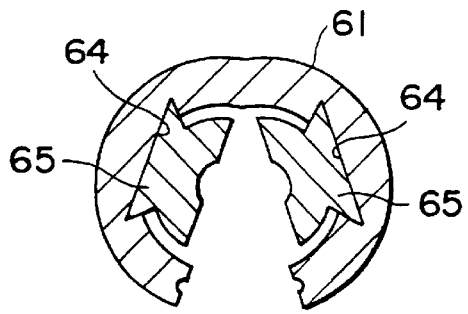

If the operator pulls the breaking wire 53 when the head 61 reaches the stomach of the patient, part of the head 61 and part of the sheath 1B are broken (FIG. 21D).

Figure 22:
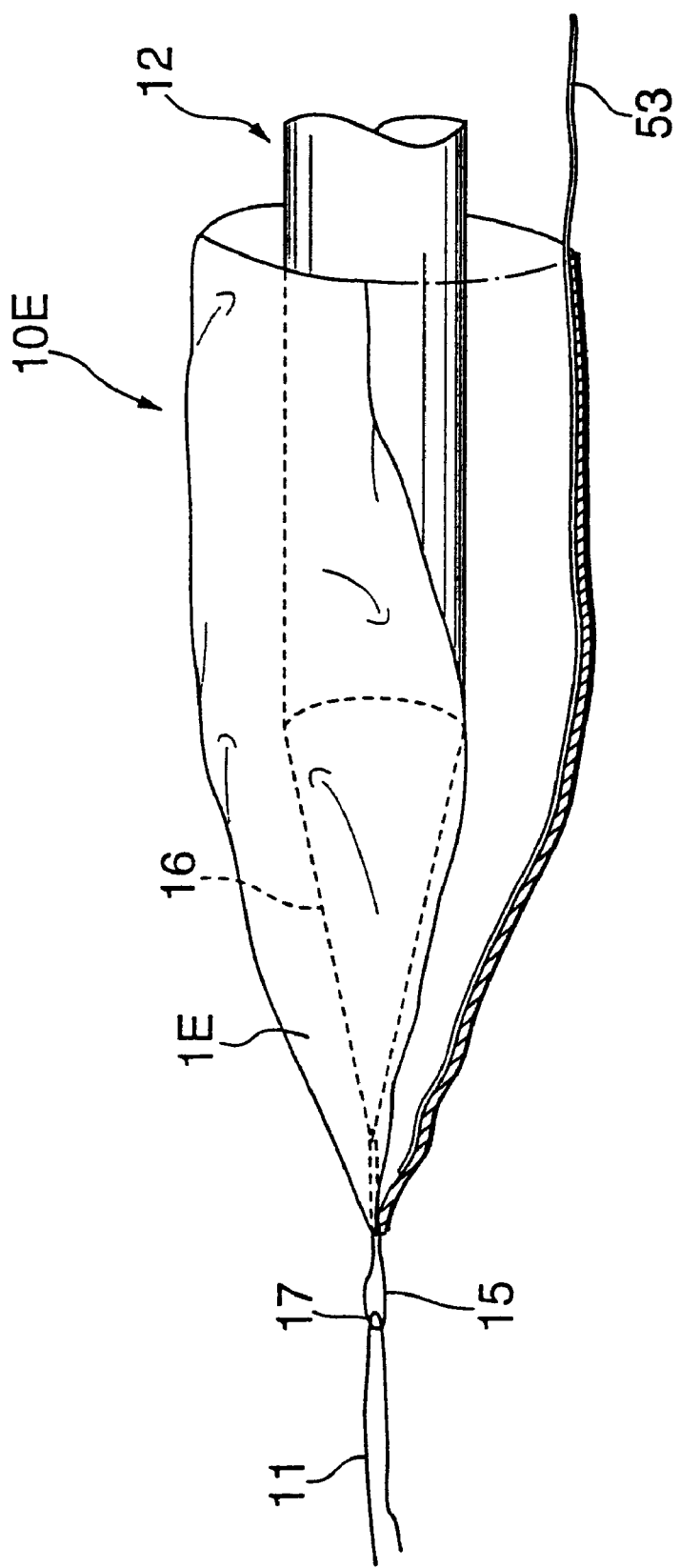
FIG. 22 is a partially cut-away perspective view showing still another example of a PEG catheter kit.

FIG. 22 shows further example of a PEG catheter kit. An infection preventive cover 10E comprises a sheath 1E and a breaking wire 53. The top of the sheath 1E is tapered to be closed at a position of the joint wire 15 extended from the taper section 16 of the PEG catheter 12. A part of the joint wire 15 is outside the sheath 1E, so that the joint wire 15 can be coupled with the guide wire 11. Preferably the exposed portion of the point wire 15 is sufficiently disinfected.

A breaking wire 53 extends to the top portion of the sheath 1E along the inner surface of the sheath 1E to be adhered or melted to the inner surface of the sheath 1E. Preferably, a portion of the sheath 1E, on which the breaking wire 53 is adhered, is weakened. For example, a part of the sheath 1E is cut, the breaking wire 53 is adhered to along the cut lines, and the cut lines of the sheath 1E is melted to be adhered to each other together with the breaking wire 53. The other end of the breaking wire 53 is led outside of the sheath 1E.

When the top (the taper section 16) of the PEG catheter 12 covered with the sheath 1E reaches the stomach of the patient, if the operator pulls the braking wire 53 in the side of the mouth of the patient, the top portion of the sheath 1E is broken.

Second Embodiment

Figure 24:
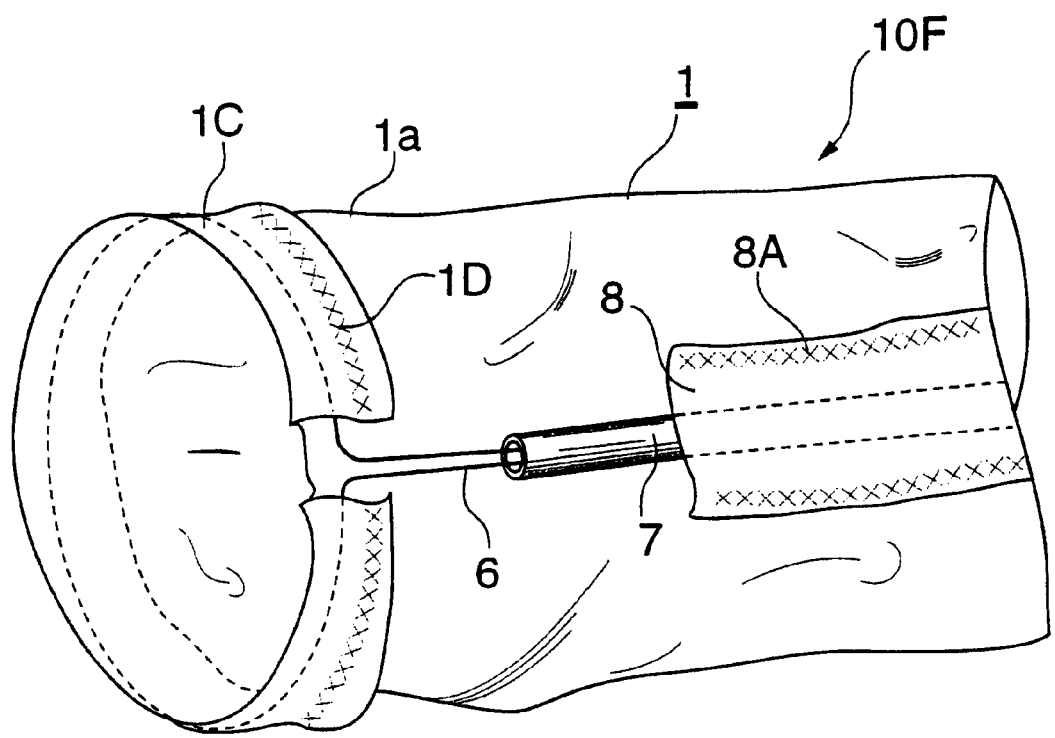
FIG. 24 is an enlarged perspective view of a portion of an infection preventive cover.
Figure 25:
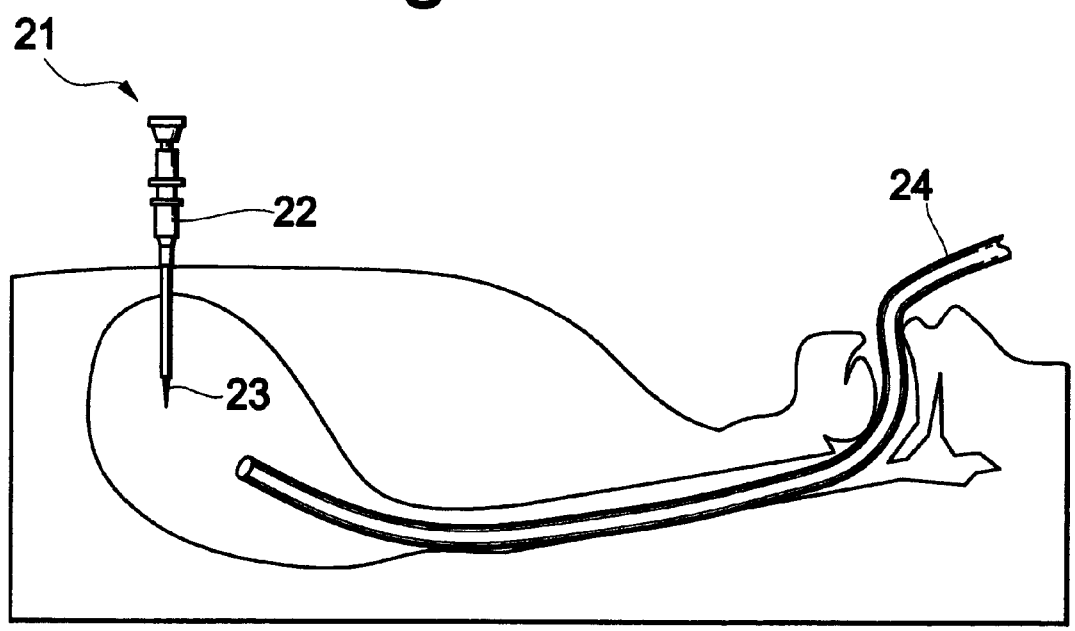
FIG. 25 is a cross-sectional view schematically showing an upper half of a body of a patient in which a endoscope is inserted in the body in a PEG process.
Figure 26:
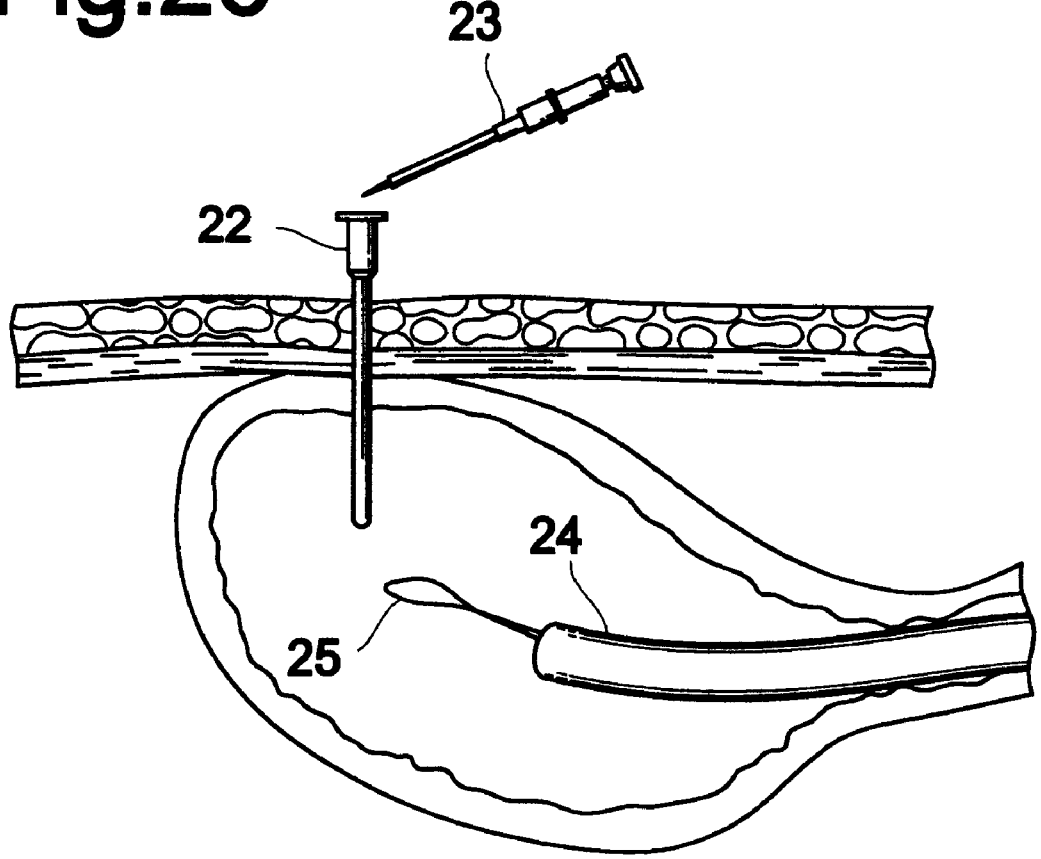
FIG. 26 is a cross-sectional view shematically showing an enlarged part of a stomach of a patient in which a endoscope is inserted in the body in a PEG process.

FIG. 23 shows an infection preventive cover 10F of the second embodiment used in a percutaneous endoscopic gastrostomy (PEG). FIG. 24 shows a top end portion of the infection preventive cover 10F in an enlarged form. In these drawings, the same reference numerals are assigned to the same elements as those shown in FIGS. 1 and 16 in order to avoid overlapped explanation.

Preferably in the same way as shown in FIG. 16, the circumferential periphery portion 1C of the opening end 1*a* of the sheath 1 is folded back outside and the folded-back portion 1C is melted (or welded or adhered) at its edge to the sheath 1 (the adhered portion is indicated by a reference numeral 1D) to form a bag, a path or a guide along the edge of the opening end of the sheath 1. The circumferential periphery portion 1C of the opening end of the sheath may be folded back inside. A closing thread or string 6 is passed through the bag, path or guide. Both ends of the closing thread 6 are outwardly led from the circumferential peripheral of the sheath 1 at positions near to each other.

The sheath 1 is provided with a cover 8 on the outer surface thereof along the longitudinal direction of the sheath. Preferably the cover 8 is also made of a thin, air-tight, water proof, flexible and strong material such as vinyl or a rubber. The cover 8 is melted (or welded or adhered) to the outer surface of the sheath at both sides thereof (the adhered portion is indicated by a reference numeral 8A) to form a bag, path or guide along the longitudinal direction of the sheath. The cover 8 extends from the vicinity of the opening end 1a of the sheath 1 to the vicinity of the another end 1b of the sheath, or to a position between the center of the sheath and the another end 1b of the sheath 1. The length of the cover 8 may be the length from the stomach to the oral cavity of a patient.

A slender tightening tube (a tube for tightening, fastening, straining, pulling or pushing) is passed through the bag, path or guide formed by the outer surface of the sheath 1 and the cover 8. The tightening tube 7 is longer than the cover 8. The tightening tube 7 is movable in the longitudinal direction of the sheath 1, since the tube 7 is just passed through the bag, path or guide. The closing thread 6 (or its two portions led outside from the bag, path or guide formed along the edge of the opening end of the sheath 1) is (are) entered into the tightening tube 7 at its one end, loosely passed through the tightening tube 7 and led outside from another end of the tightening tube 7. The one end of the tightening tube 7 is positioned in the vicinity of the opening end of the sheath 1.

The tube 7 is made of a material such as a plastic or other flexible materials. For easily to understand, the tightening tube 7 is depicted somewhat largely in diameter. The tightening tube 7 is a slender (thin) and long tube having a long hole formed therein, and the long hole allows the closing thread 6 to loosely pass.

Both end portions of the closing thread 6 which are led outside from the tightening tube 7 pierce (enter into) a clamping member (a member for preventing from being loosened) 9 at one side surface thereof and come out (or appear) from the other side surface of the clamping member 9, and again enter into the clamping member 9 at the other side surface thereof and led outside from the one side surface of the clamping member 9. That is, the two closing threads (or two end portions of the closing thread) 6 are tightly pierced (passed) the clamping member 9 twice.

Preferably the clamping member 9 is made of an elastic material such as a silicon rubber. The closing thread 6 which is passed through the elastic material is kept (maintained) in its position (with hardly moving) by a friction force produced between the elastic material and the closing thread 6.

A silk thread is utilized as the closing thread 6. For the closing thread 6, there may be employed threads respectively made of linen, cotton, polyester, polyethylene, and any other vegetable or chemical fiber.

Referring now to FIGS. 25 to 35, description will be given in detail of a usage method and a role of the infection preventive cover 10F configured as above in relation to the PEG method. In this example, a method called "pull method (technique)" will be described. The PEG method is performed in general by an operator, an endoscopist and one or two nurses.

Figure 27:
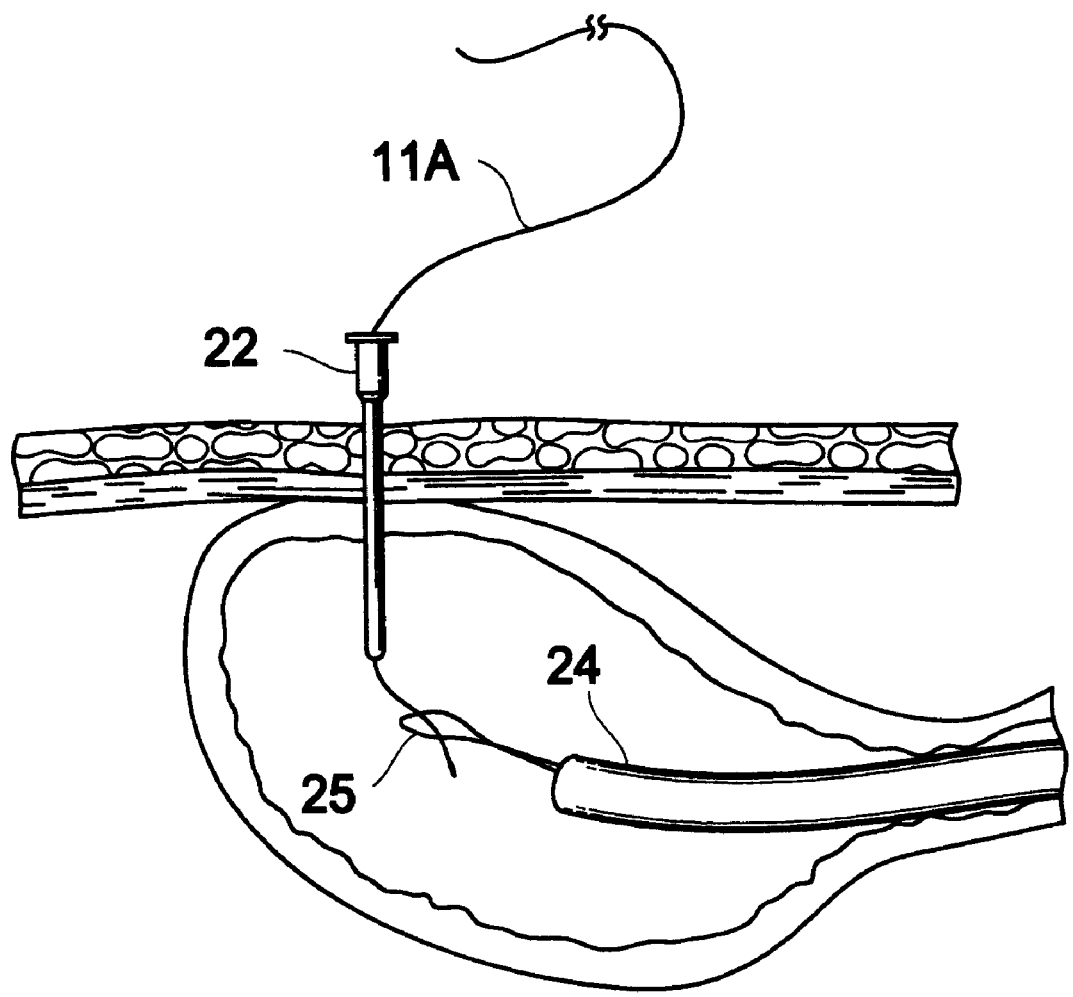
FIG. 27 is a cross-sectional view schematically showing a part of a stomach of a patient in which a guide wire is inserted into the stomach in a PEG process.

As can be seen from comparison between FIGS. 2 to 4 and FIGS. 25 to 27, the same procedure is taken as the first embodiment, that is, insertion of an endoscope 24 and piercing of a needle 21 (FIG. 25), removal of a needle 23 (FIG. 26), and an insertion of a guide wire 11A (FIG. 27).

An end of the guide wire 11A fed into the stomach is grasped by the snare forceps 25. The guide wire 11A held by the snare forceps 25 is withdrawn out of the oral cavity of the patient together with the endoscope 24. After the guide wire 11A is sufficiently drawn out of the oral cavity, the snare forceps 25 is released from the guide wire 11A.

Figure 28:
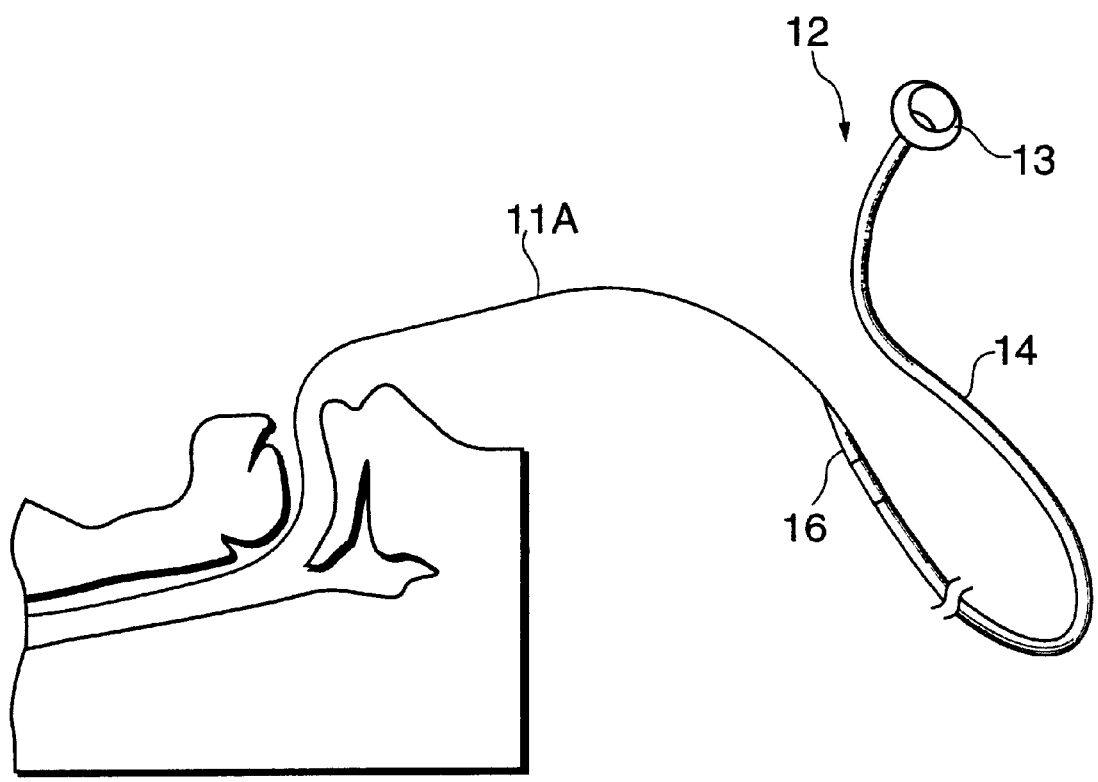
FIG. 28 is a perspective view showing a linkage between a guide wire and a joint wire in a PEG process.

The PEG catheter 12 includes a PEG tube 14 which has a top end portion tapered in a cone shape (conical shaped top portion) (this section is called a taper section 16) and which has another end at which a dome 13 is integrally coupled with or connected to. The taper section 16 of the PEG catheter 12 and the guide wire 11A drawn out of the oral cavity is coupled with point to) each other (FIG. 28). The coupling will be described later along with the structure of the taper section 16.

Figure 29:
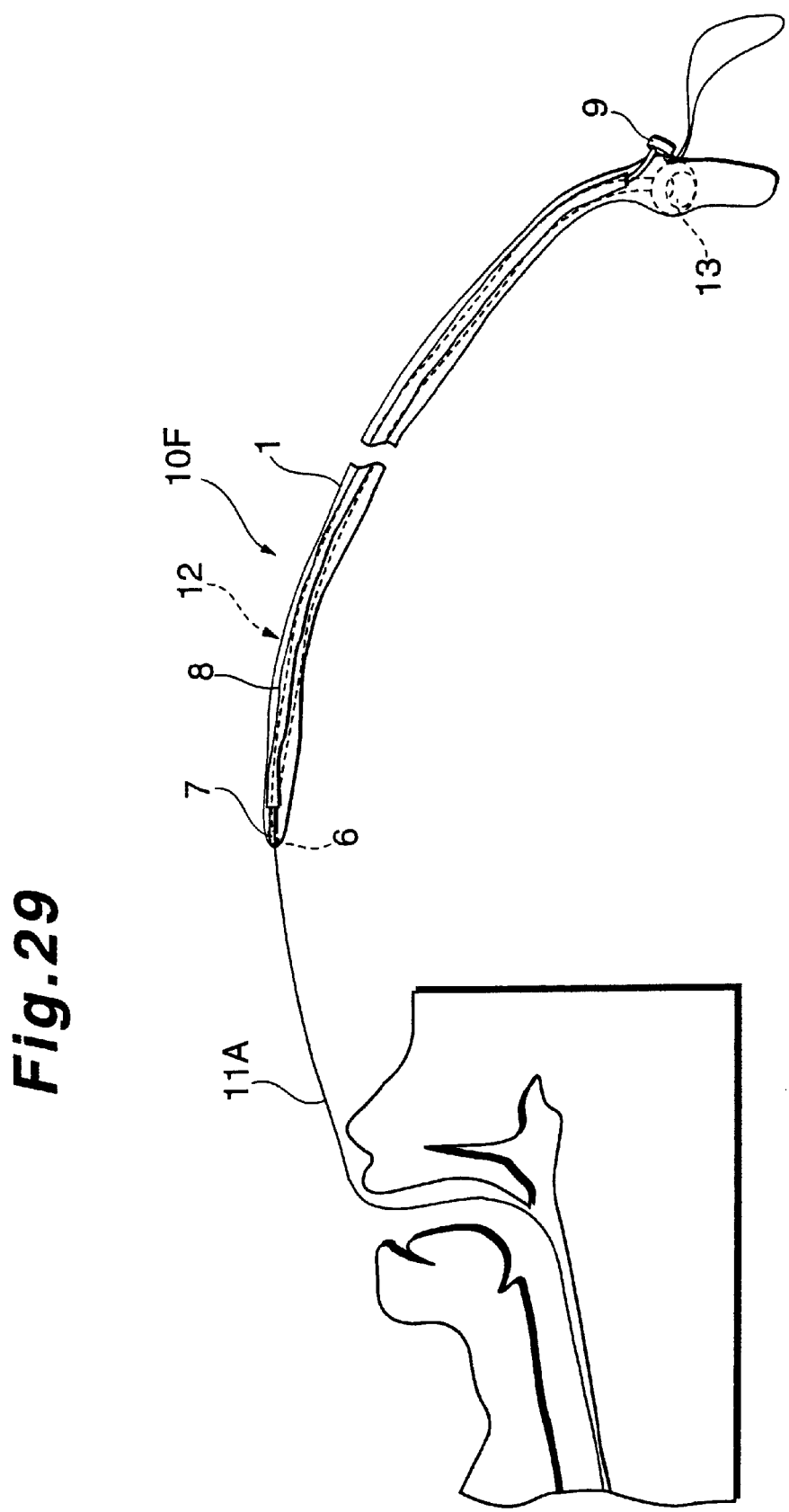
FIG. 29 is a cross-sectional diagram schematically showing a portion ranging from a head to an upper pharyrnx of a patient in a PEG process.

The whole of the PEG catheter 12, i.e., the portion ranging from the dome 13 to the taper section 16 is inserted into the sheath 1 of the infection preventive cover 10F and the opening end 1a of the sheath 1 is closed using the closing thread 6. The PEG catheter 12 inclusive of the taper section 16 is covered by the sheath 1 (FIG. 29).

Figure 35:
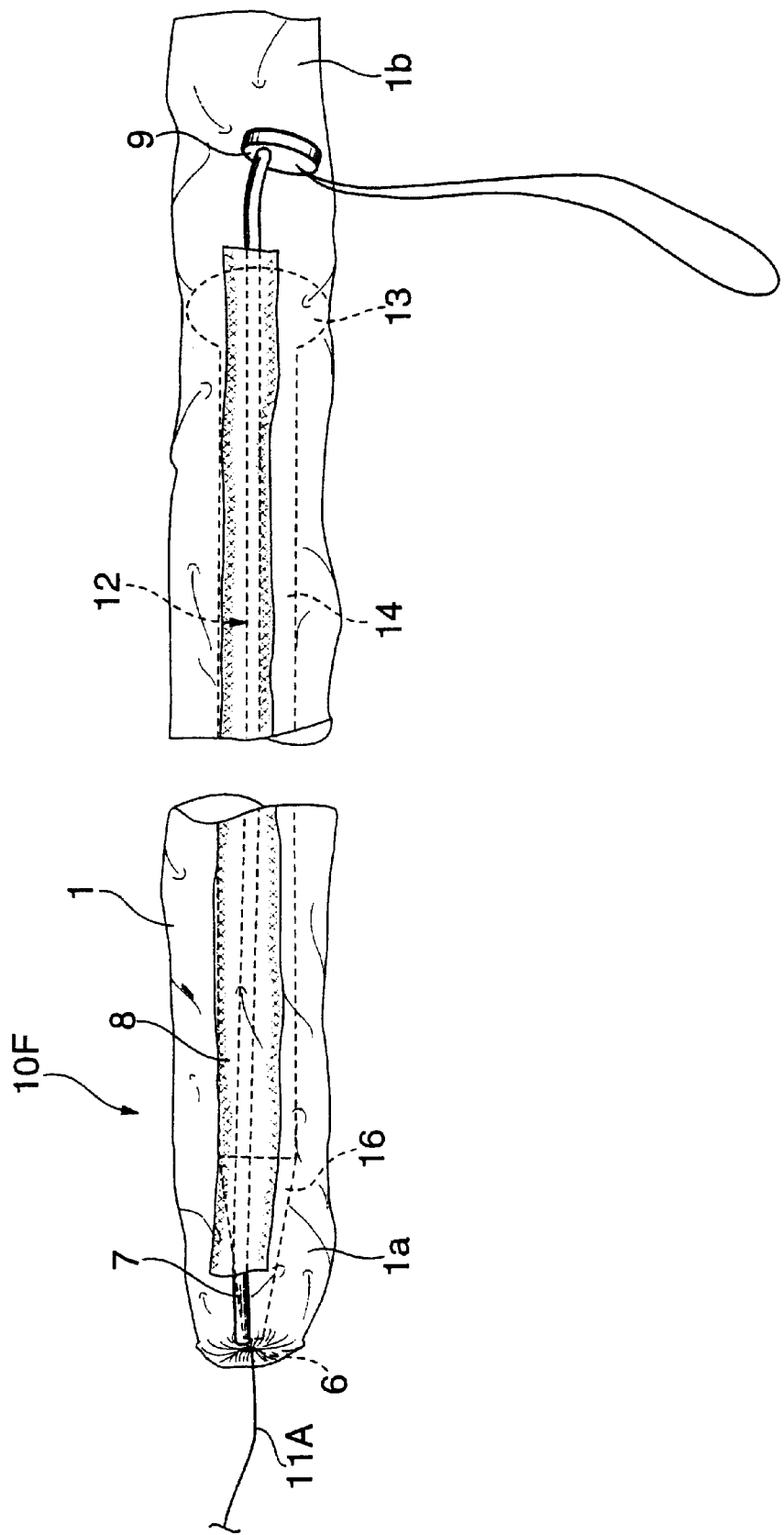
FIG. 35 is a perspective view showing a state in which a PEG catheter is covered with an infection preventive cover.

FIG. 35 shows in an enlarged diagram, a state in which the opening end 1a of the sheath 1 of the infection preventive cover 10F is closed by the closing thread 6.

Both ends of the closing thread 6 which have been led outside from the another end of the tightening tube 7 are pulled and the tightening tube 7 is pushed, so that the one end of the tightening tube 7 approaches the opening end of the sheath 1. A loop formed by the closing thread 6 becomes small and the opening end 1a of the sheath 1 is tightened or fastened by the closing thread 6 and the one end of the tightening tube 7 so that the opening end 1a is closed (the closed opening-end 1a of the sheath 1 is referred to as a "closed end" hereinafter). The closing thread 6 is embroidered in the closed end of the sheath 1. The clamping member 9 is moved along the closing thread portion 6 toward the another end of the tightening tube 7. The opening end 1a (closed end) of the sheath 1 is kept in its closed state by elasticity of the clamping member 9 and a friction force produced between the clamping member 9 and the closing thread 6, even the operator release his or her hold of the tightening tube 7 and the closing thread 6.

Figure 40A:
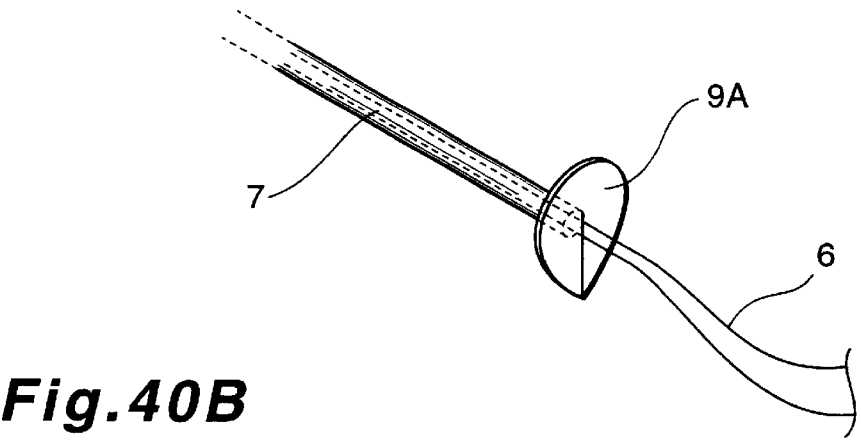
FIGS. 40A to 40C show another examples of a clamping member.
Figure 40B:
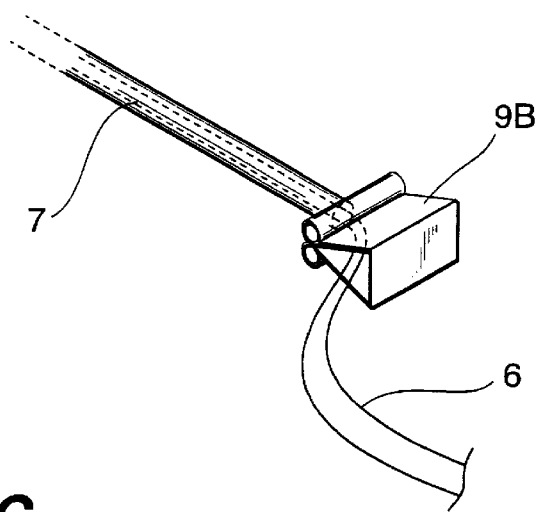
Figure 40C:
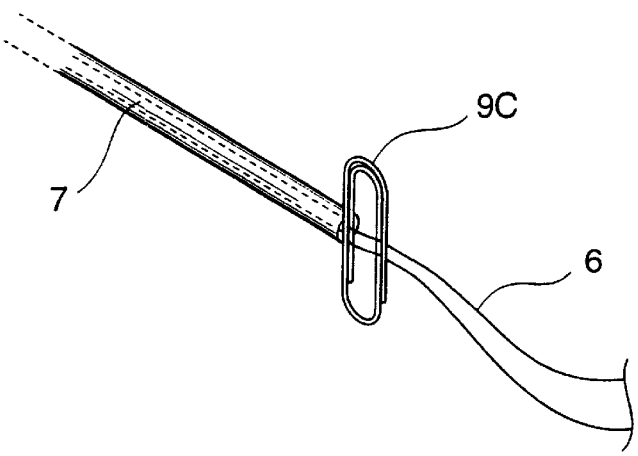

FIGS. 40A to 40C show another examples of the clamping member. The closing thread 6 is prevented from being loosened by inserting the closing thread 6 into the slit formed on the clamping member 9A as shown in FIG. 40A, or by clipping the closing thread 6 using a clip 9B or 9C as shown in FIG. 40B or 40C.

Figure 30:
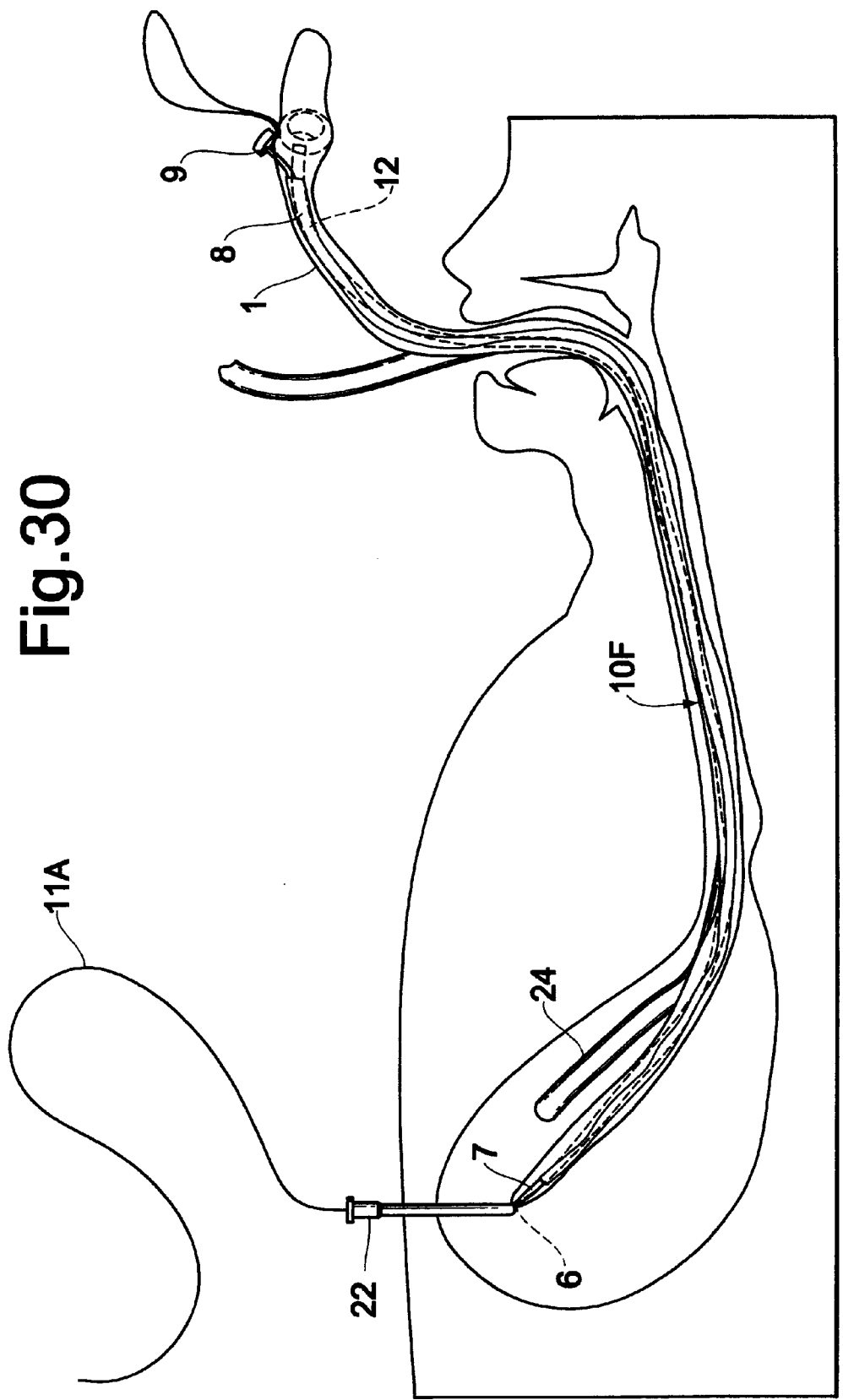
FIG. 30 is a cross-sectional view schematically showing an upper half of a body of a patient in which a PEG catheter covered with an infection preventive cover is pulled in a PEG process.

The end of the guide wire 11A drawn through the outer tube 22 into a space outside the body of the patient is pulled. This causes the PEG catheter 12 coupled with the guide wire 11A to be delivered through the oral cavity, the upper pharynx and the larynx into the stomach with the catheter 12 covered with the sheath 1 (FIG. 30).

At the same time, the endoscope 24 is again inserted through the oral cavity into the stomach. By inserting the endoscope 24 along the PEG catheter, it is possible to smoothly move the endoscope 24 into the stomach of the patient.

Figure 31:
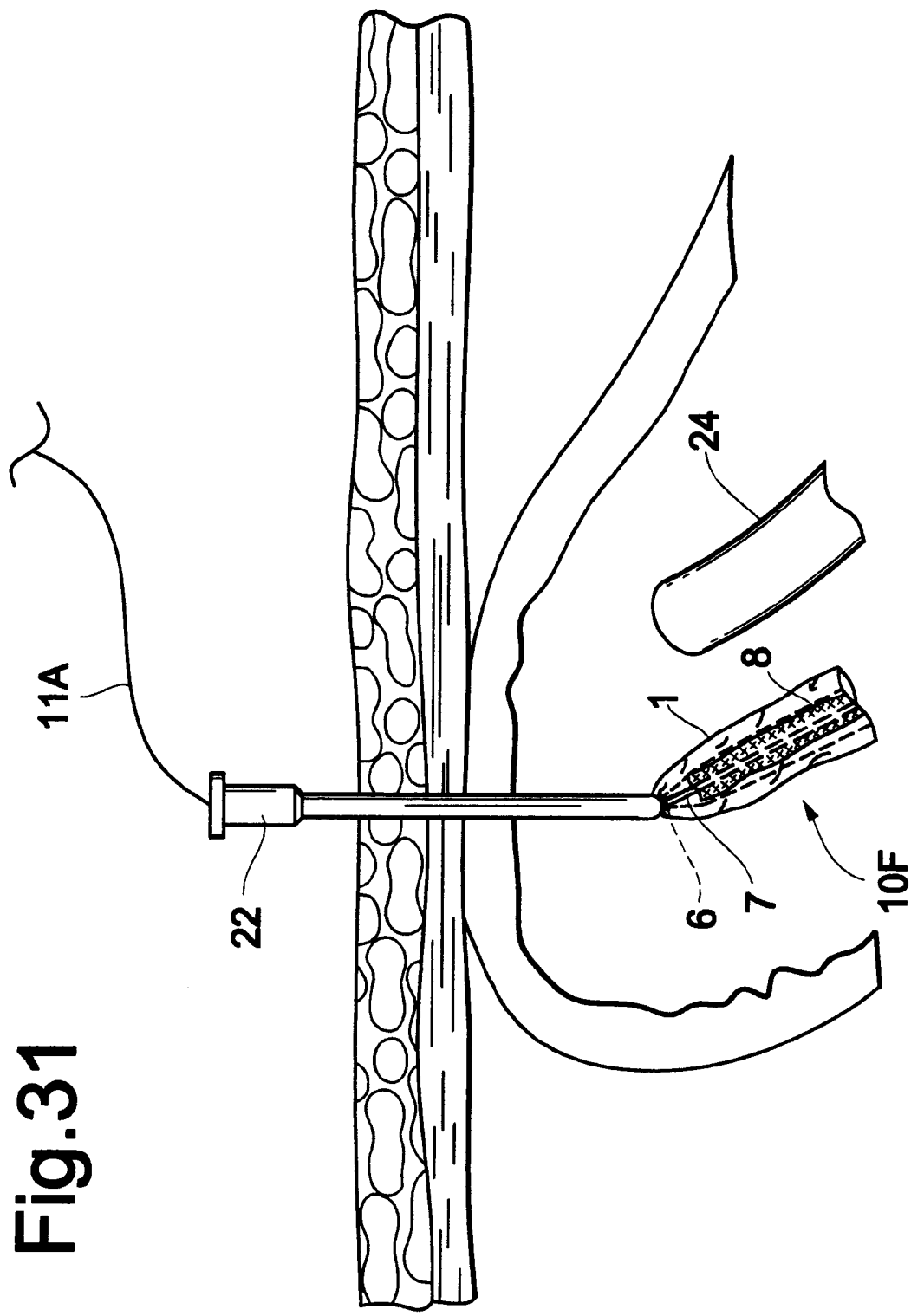
FIG. 31 is a cross-sectional view schematically showing an enlarged part of a stomach of a patient in which a PEG catheter covered with an infection preventive cover is pulled in a PEG process.

When the guide wire 11A is further drawn, the closed end of the sheath 1 abuts on an end of the outer tube 22 (FIG. 31). It is favorable to confirm this event, i.e., the closed end of the sheath 1 abuts on the end of the outer tube 22 by the endoscope 24. In this state, the PEG catheter 12 and another end of the sheath 1 are still outside the mouth of the patient (FIG. 30). It may also be favorable to confirm by a hand that the closed end of the sheath 1 abuts on the end of the outer tube 22. It may thereafter be possible to insert the endoscope 24 into the stomach. The second insertion of the endoscope 24 may be avoided.

Figure 32:
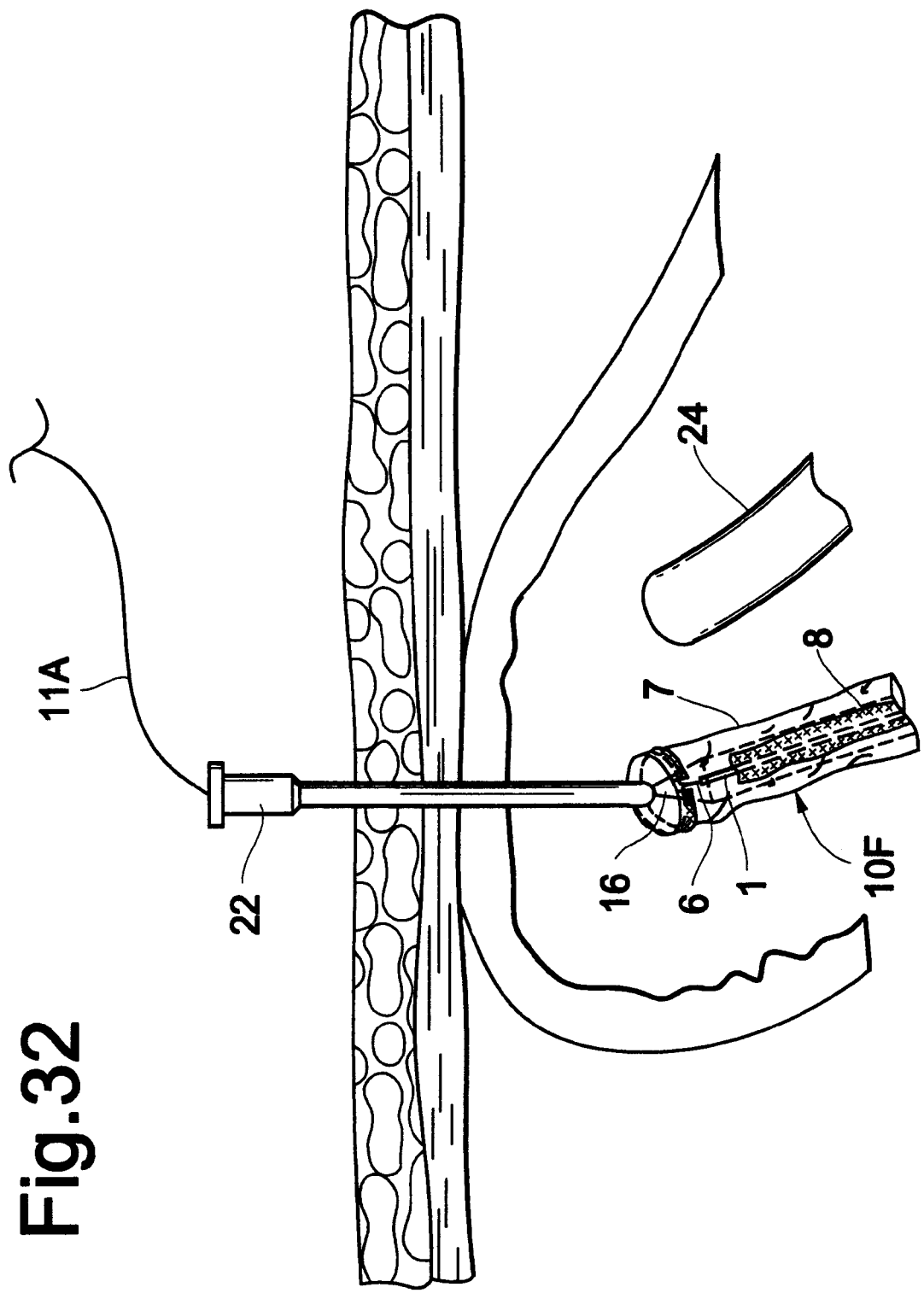
FIG. 32 is a cross-sectional view schematically showing an enlarged part of a stomach of a patient in which an opening end of a sheath is opened in a PEG process.

The clamping member 9 is moved in the direction that the clamping member 9 is separated (apart) from the another end of the tightening tube 7, i.e., in the direction toward the both ends of the closing thread (portions) 6, and the tightening tube 7 is moved so as to get away from the closed end of the sheath 1. Thus, the closing thread 6 is loosened and the closed end of the sheath is opened or become openable state (FIG. 32).

It is desirable that the opening end 1a of the sheath 1 is beforehand prepared to easily open outwardly, for example, by bending the opening end 1a several times or by giving nature to open. With this preparation, it is guaranteed that the sheath 1 opens when the closing thread 6 is loosened.

Figure 33:
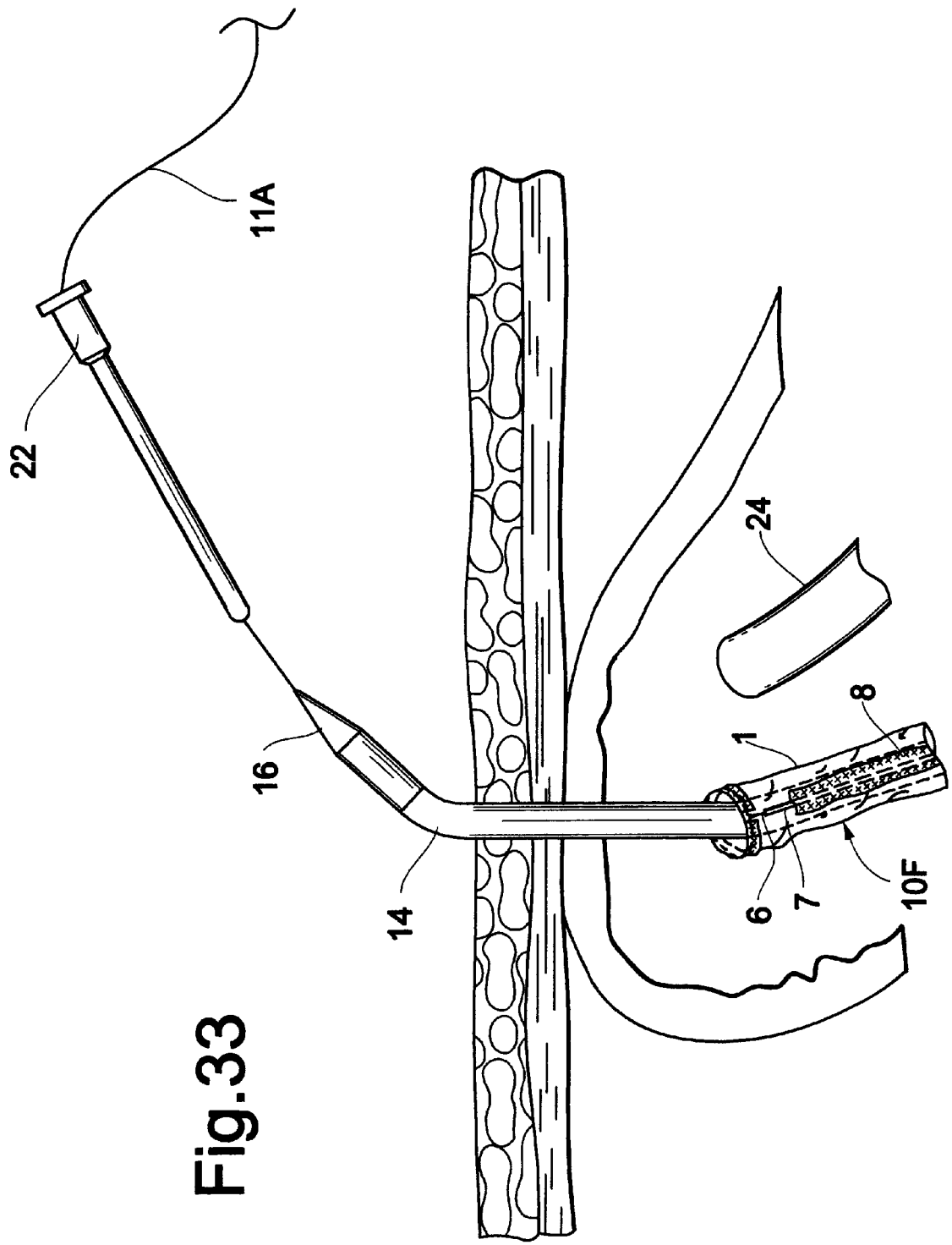
FIG. 33 is a cross-sectional view schematically showing an enlarged part of a stomach of a patient in which a PEG catheter is drawn out of a body in a PEG process.

While the outer tube 22 is being drawn through the stomach and abdomen walls, the guide wire 11A is further withdrawn outwardly. The taper section 16 and the PEG tube 14 are delivered through the stomach wall and the abdomen wall into a space outside the patient body (FIG. 33).

When the PEG catheter 12 is being drawn toward the outside of the patient body, the endoscopist holds by a hand the end 1b of the sheath 1 outside the mouth of the patient such that the sheath 1 is not fed into the patient body.

Figure 34:
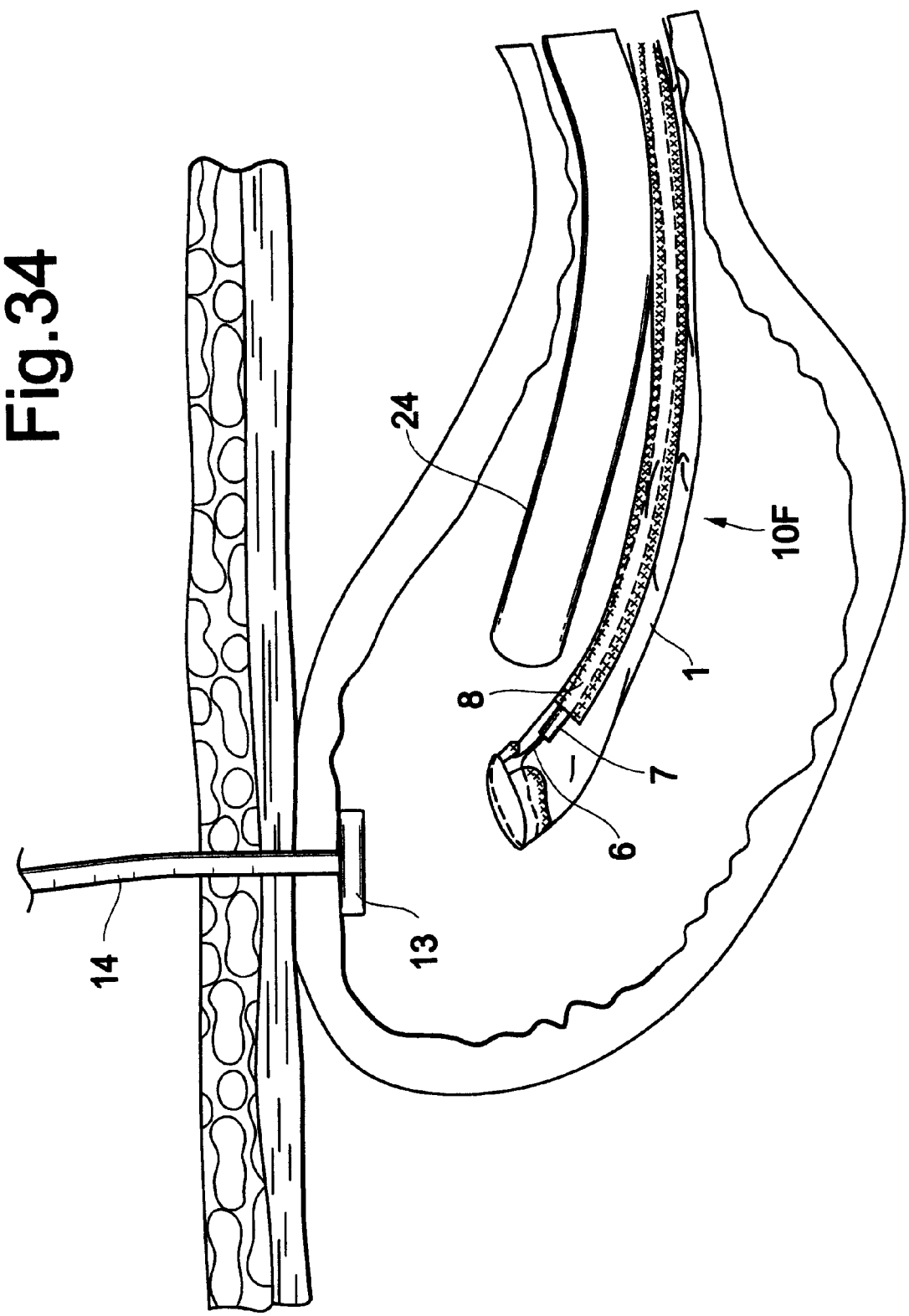
FIG. 34 is a cross-sectional view schematically showing a part of a stomach of a patient in which a dome at an end of a PEG catheter abuts on a stomach wall in a PEG process.

Finally, the dome 13 appears from the opening end of the sheath 1 and abuts on the stomach wall (FIG. 34). If necessary, this condition that the dome 13 abuts on the stomach wall is confirmed by the endoscope 24. The sheath 1 is removed from the mouth of the patient into a space outside the patient.

The PEG tube 14 thus withdrawn is cut at an appropriate point to have a necessary length, and the cut-off end is connected with an adapter to supply a medicine for nutrition. The PEG tube is attached onto the body of the patient with an appropriate fixing unit (means), thereby completing the operation of the PEG method.

Outer surfaces of the guide wire 11A and the sheath 1 having passed through the larynx, the upper pharynx and the oral cavity are infected by bacteria on the oral cavity, the upper pharynx and the larynx. However, since the guide wire 11A is drawn through the outer tube 22 into a space outside the patient body, it hardly occurs that the wound (hole) in the stomach and abdomen walls is infected by the guide wire 11A. Furthermore, the taper section 16, the PEG tube 14 and the dome 13 are each covered with the sheath 1 to be fed, in this state, through the oral cavity, the upper pharynx and the larynx into the stomach to be then withdrawn from the sheath 1 in the stomach. Even when the taper section 16 and the PEG tube 14 are brought into contact with the wound when they are drawn to a space outside the patient, there is almost no chance that the wound is contaminated by bacteria. The sheath 1 of which outer surfaces are infected are removed through the mouth of the patient. It does not occur that the wound is infected by the infection preventive cover 10F. In consequence, the infection of the wound can be advantageously prevented.

Also in the "push" method, it is possible to effectively prevent infection of the wound by pushing the PEG catheter 12 covered with the infection preventive cover 10F into the stomach.

No special skill is required for closing the opening end and for opening the closed end using the closing thread 6 and the tightening tube 7. The time required for gastrostomy is shortened.

Figure 38:
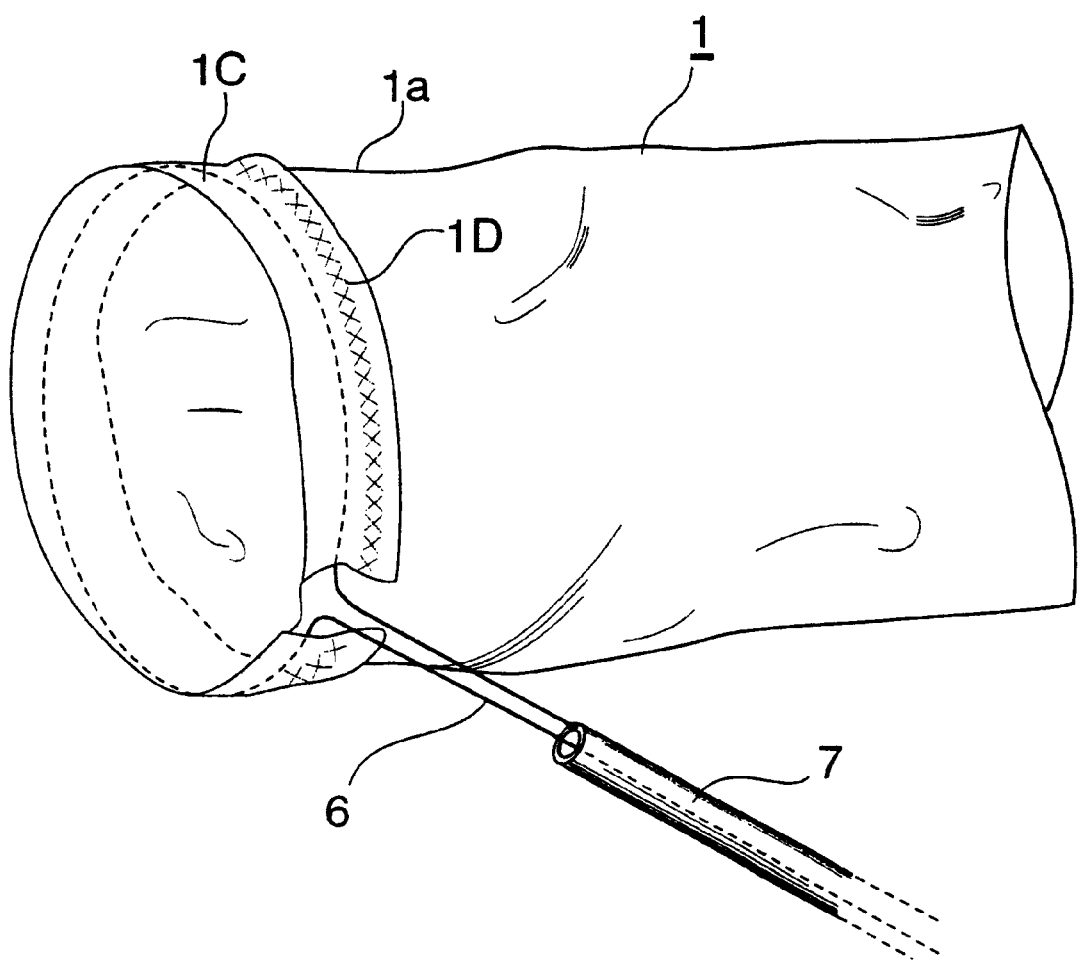
FIG. 38 is a enlarged portial perspective view showing another example of an infection preventive cover with a closing thread embroidered thereon.
Figure 39:
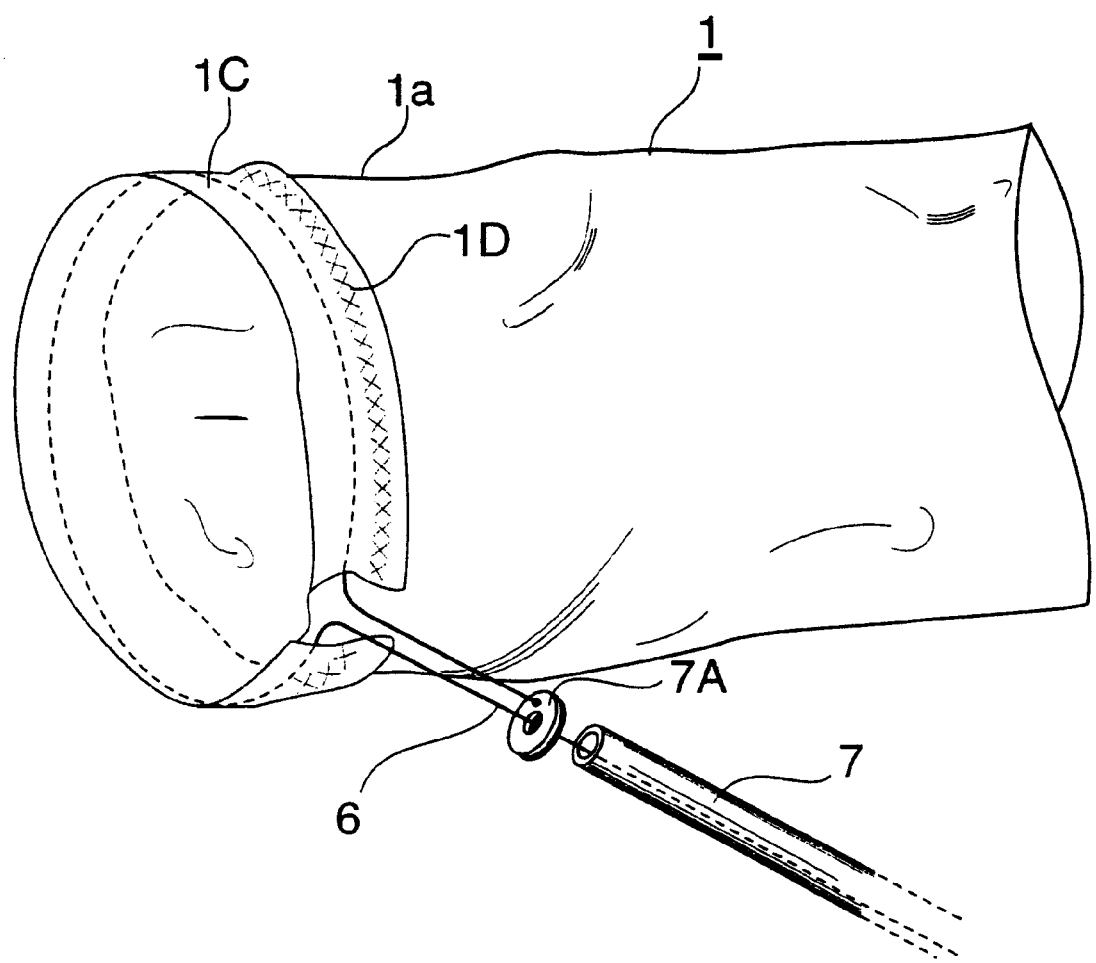
FIG. 39 is a enlarged portial perspective view showing still another example of an inflection preventive cover with a closing thread embroidered thereon.

Both end portions of the closing thread 6 (two closing thread portions) are not necessarily drawn outside of the tightening tube 7. As shown in FIG. 38, one end of the closing thread 6 may be fixed to the end of the tightening tube 7 by adhering or welding, and another end portion of the closing thread 6 may be passed through the tightening tube 7 to be drawn outside. Alternatively, as shown in FIG. 39, one end of the closing thread 6 may be fixed to a ring 7A having a hole by adhering or welding, and another end portion of the closing thread 6 may be loosely passed through the hole of the ring 7A and further passed through the tightening tube 7 to be drawn outside. In either embodiment shown in FIG. 38 or 39, it is easy to make it possible to close the opening end of the sheath or to open the closed end using the closing thread 6 and the tightening tube 7.

The infection preventive cover 10F can be applied also to the button-type PEG catheter including the one-step button as shown in FIG. 17. It is also to be understood that the infection preventive cover 10F is applicable to PEG catheters in another configuration.

FIGS. 36A to 36C and FIGS. 37A to 37C show details of the connection (joint or link) between the PEG catheter and the guide wire.

The guide wire 11A which is drawn from the oral cavity of the patient is formed with a spherical shaped head 11a at the top end thereof The taper section 16 of the PEG catheter 12 is hollow (inside space is indicated by numerical reference 16a) and is formed with an opening (a hole) 16e at the top end thereof, the opening 16e allowing the head 11a to pass therethrough. The top end portion (including the head 11a) of the guide wire 11A which is drawn from the oral cavity is inserted into the inside of the taper section 16 through the opening 16e.

The taper section 16 is provided with a plate (engaging piece) 16b inside thereof near the boundary portion between the taper section 16 and the PEG tube 14, the plate 16b being obliquely disposed (fixed) with respect to the axial direction of the taper section 16. The obliquely disposed plate 16b has a wide slit 16c formed on the one-half portion of the plate 16b (upper half portion, i.e., the portion directed to the PEG tube 14), the wide slit 16c having width which allows the head 11a of the guide wire 11A to pass therethrough. The width of the slit 16c is narrowed at the center of the plate 16b. The plate 16b is formed with a narrow slit 16d on the other half portion (a portion directed to the opening 16e of the taper section 16), the narrow slit 16d is coupled to (connected to) the wide slit 16c (see FIGS. 36A and 37A).

Figure 36A:
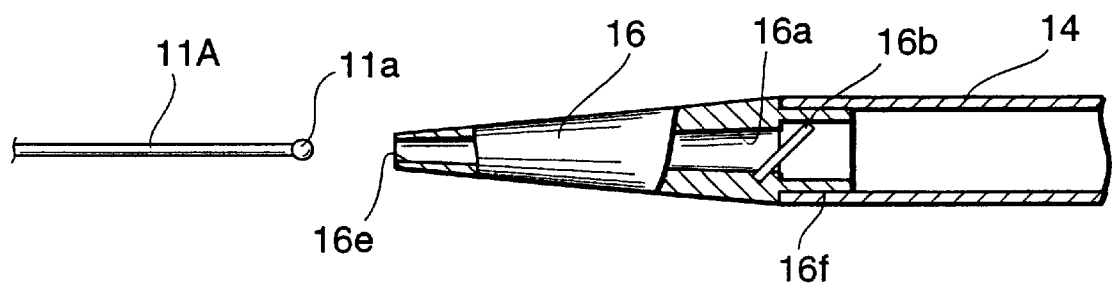
Figure 36B:
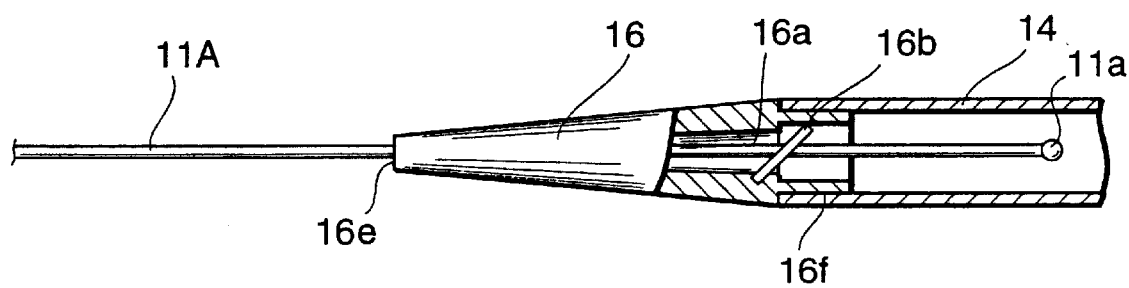
Figure 36C:
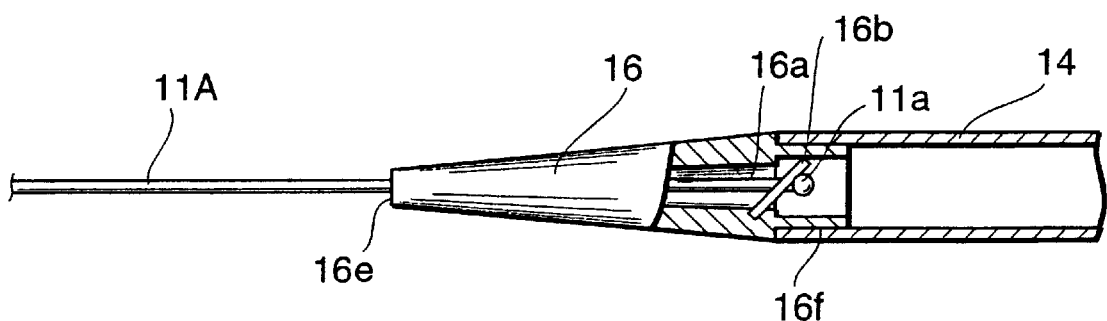
Figure 37A:
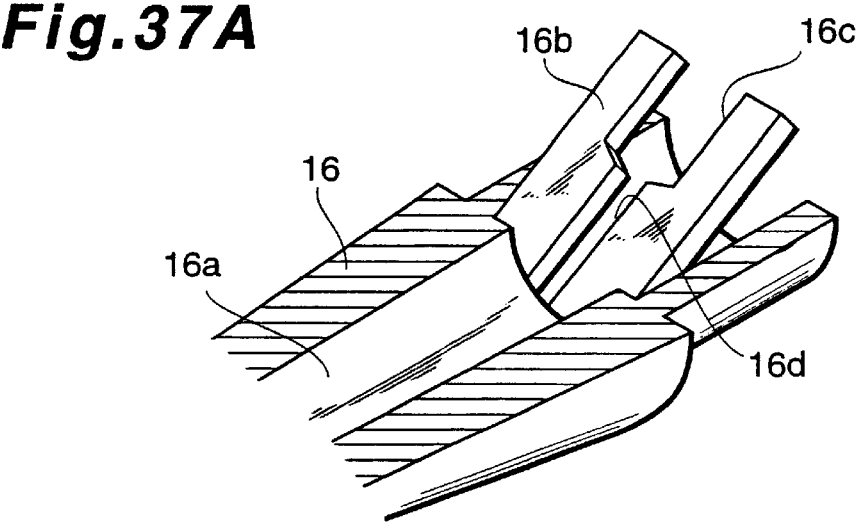
Figure 37B:
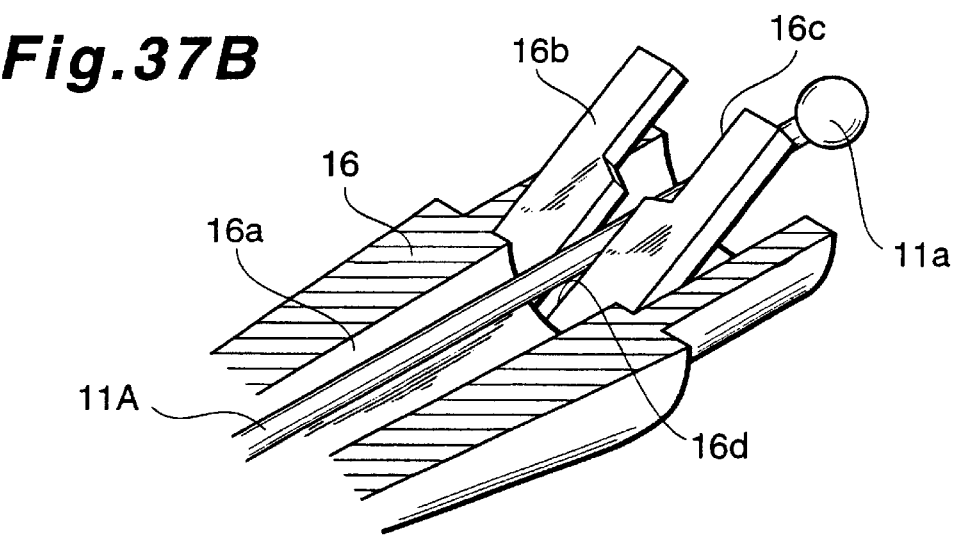
Figure 37C:
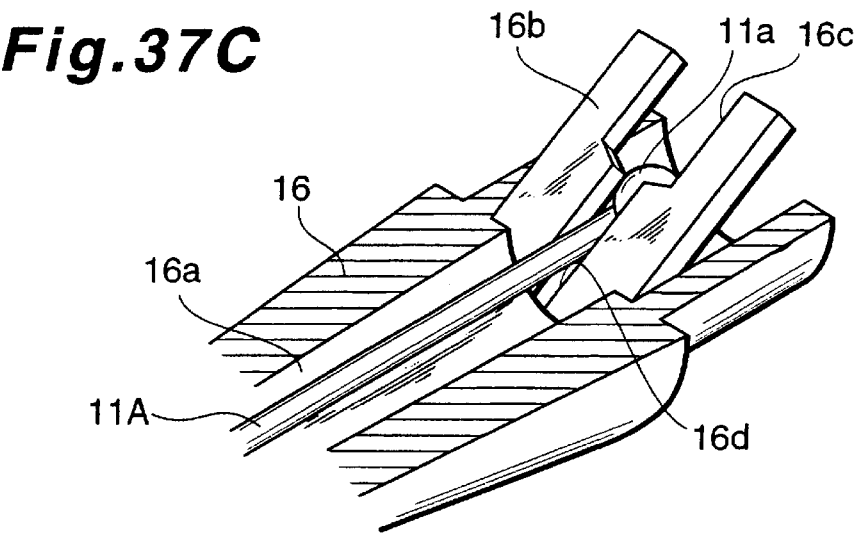

When the guide wire 11A is inserted into the inside of the taper section 16 through the opening 16e, the spherical head 11a formed at the top end of the guide wire 11A passes through the wide slit 16c of the plate 16b, and proceeds to the PEG tube 14 side over the position of the plate 16b. The guide wire 11A enters (falls down) the narrow slit 16d of the plate 16b (FIGS. 36B and 37B). In this state, even if the guide wire 11A is pulled, the head 11a engages with the narrow slit 16d, so that the guide wire 11A is prevented from being pulled out or drawn out (FIGS. 36C and 37C). In this way, the PEG catheter 12 and the wire guide 11A are linked to each other.

The taper section 16 is formed with a step 16f at end thereof and an end of the PEG tube 14 is fitted to the step 16f to be fixed.

While the present invention has been described with reference to the particular illustrative embodiments, it is not to be restricted by those embodiments but only by the appended claims. It is to be appreciated that those skilled in the art can change or modify the embodiments without departing from the scope and spirit of the present invention.

What is claimed is:

1. An infection preventive cover kit, comprising:
   a sheath having at least one opening end;
   a binding thread to close the opening end of the sheath; and
   a cutting thread linked to the binding thread, the cutting thread being stronger than the binding thread.

2. An infection preventive cover comprising:
   a sheath having at least one opening end;
   a binding thread having two ends, said binding thread embroidered along a circumferential edge of said at least one opening end of the sheath; and
   a cutting thread linked to the binding thread,
   wherein the two ends of the binding thread are outside the sheath at positions near to each other, and the cutting thread is stronger than the binding thread.

3. A percutaneous endoscopic gastrostomy catheter kit, comprising:
   a percutaneous endoscopic gastrostomy catheter;
   a sheath, into which the catheter has been inserted, having at least one opening end;
   a binding thread to close the opening end of the sheath; and
   a cutting thread linked to the binding thread, the cutting thread being stronger than the binding thread.

4. The catheter kit according to claim 1, wherein the binding thread includes first and second ends, and is embroidered along a circumferential edge of the opening end of the sheath, and
   wherein said first end and said second end of the binding thread are led outside the sheath at positions near to each other.

* * * * *